US005705188A

United States Patent [19]

Junichi et al.

[11] Patent Number: 5,705,188
[45] Date of Patent: Jan. 6, 1998

[54] DRUG COMPOSITION CONTAINING NUCLEIC ACID COPOLYMER

[75] Inventors: Yano Junichi, Nara; Tadaaki Ohgi, Otsu, both of Japan

[73] Assignee: Nippon Shinyaku Company, Ltd., Japan

[21] Appl. No.: 507,269

[22] PCT Filed: Feb. 17, 1994

[86] PCT No.: PCT/JP94/00238

§ 371 Date: Oct. 10, 1995

§ 102(e) Date: Oct. 10, 1995

[87] PCT Pub. No.: WO94/18987

PCT Pub. Date: Sep. 1, 1994

[30] Foreign Application Priority Data

Feb. 19, 1993 [JP] Japan ................................ 5-054939

[51] Int. Cl.$^6$ ........................................... A61K 9/127
[52] U.S. Cl. ............................ 424/450; 424/461; 514/44; 560/224
[58] Field of Search ..................... 424/450, 461; 514/44; 560/224; 935/24, 34, 54

[56] References Cited

U.S. PATENT DOCUMENTS

| 4,797,479 | 1/1989 | Shuto et al. ............... 536/27 |
| 4,882,147 | 11/1989 | Bardos et al. ............ 424/85.4 |
| 5,231,085 | 7/1993 | Alexander et al. ........ 514/44 |

FOREIGN PATENT DOCUMENTS

| 299082 | 1/1989 | European Pat. Off. |
| 468520 | 1/1992 | European Pat. Off. |

OTHER PUBLICATIONS

Alberts, B et al. Molecular Biology of the Cell, second edition. p. 98. Garland Publishing, New York, 1989.
Yu, ACH et al. Inhibition of GFAP synthesis by antisense RNA in astrocytes. J. Neuroscience Res. 30:72–79, 1991.
Magee, WE, et al. A comparison of negatively and positively charged liposomes containing entrapped polyinosinic–polycytidylic acid for interferon induction in mice. Biochim. Biophys. Acta 451:610–618, 1976.

Solodin, I. et al. A novel series of amphiphilic imidazolinium compounds for in vitro and in vivo gene delivery. Biochemistry 34:13537–13544, 1995.

Felgner, PL et al. Lipofection: a highly efficient, lipid-mediated DNA–transfection procedure. Proc. Natl. Acad. Sci. USA 84:7413–7417, Nov. 1987.

Hovanesssian, AG et al. Enhancement of natural killer cell activity and 2–5a synthetase in operable breast cancer patients treated with polyadenylic;polyuridylic acid. Cancer 55:357–362, 1985.

Derwent WPI Abstract of JP–A–3–240,795, JP–A–61–103, 824 and JP–A–59–033,222.

*Primary Examiner*—Christopher S. F. Low
*Assistant Examiner*—Dave T. Nguyen
*Attorney, Agent, or Firm*—Graham & James LLP

[57] ABSTRACT

This invention has for its object to insure an effective utilization of single-stranded nucleic acid copolymers, particularly poly(adenylic acid-uridylic acid), and to provide a pharmaceutical composition having antitumor activity.

The invention typically relates to a pharmaceutical composition comprising a lipid device such as Lipofectin (trademark), 3-O-(4-dimethylaminobutanoyl)-1,2-O-dioleylgycerol, 3-O-(2-dimethylamino-ethyl)carbamoyl-1,2-O-dioleylglycerol, 3-O-(2-diethylaminoethyl) carbamoyl-1,2-O-dioleylgycerol, or 2-O-(2-diethylaminoethyl)carbamoyl-1,3-O-dioleoylglycerol and poly(adenylic acid-uridylic acid).

10 Claims, No Drawings

DRUG COMPOSITION CONTAINING NUCLEIC ACID COPOLYMER

This application is a 35 U.S.C. 371 application of PCT/JPG4/00238 filed 17 Feb. 1994 published as WO94/18987 Sep. 1, 1994.

TECHNICAL FIELD

The present invention relates to a pharmaceutical composition characterized by comprising a lipid device and a single-stranded nucleic acid copolymer.

The term lipid device as used herein means a device comprising a natural or artificial lipid as a component thereof and having the function of promoting the intracellular uptake of a physiologically active substance.

BACKGROUND ART

Unlike a nucleic acid polymer-nucleic acid polymer complex such as polyinosinic acid-polycytidylic acid, a single-stranded nucleic acid copolymer such as poly (adenylic acid-uridylic acid) does not display interferon-inducing activity and hence, has no antitumor effect when administered alone.

Meanwhile, it is known that certain kinds of positively charged lipid devices (e.g. cationic liposomes) are instrumental to the delivery of genes into cells (e.g. JP-A-4108391, WO91/17424). It is also known that when a certain kind of nucleic acid such as a double-stranded RNA is administered together with a lipid device such as cationic liposomes, a potentiated interferon inducer action is realized (U.S. Pat. No. 5,049,386). It is generally conjectured that since the nucleic acids of, for example, genes are negatively charged, they form complexes with cationic liposomes and the complexes become fused to the cell membrane and the nucleic acids of genes or the like find their way into the cell.

However, it remains to be known whether application of a lipid device to a single-stranded nucleic acid copolymer gives rise to interferon inducer activity or an antitumor action.

DISCLOSURE OF INVENTION

The object of the present invention is to implement an effective utilization of a single-stranded nucleic acid copolymer and provide a pharmaceutical composition having antitumor activity.

In the course of intensive research, the inventors of the present invention discovered that applying a lipid device to a single-stranded nucleic acid copolymer such as poly (adenylic acid-uridylic acid) results in high interferon inducer activity and have accordingly developed the instant invention.

The lipid device that can be used includes Lipofectin (trademark, manufactured by Bethesda Research Laboratories Life Technologies Inc.) and Genetransfer (trademark, manufactured by Wako Pure Chemical Industries), which are known, and a mixture of a compound of the following general formula [I] and a phospholipid.

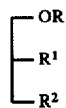

wherein $R^1$ and $R^2$ are not the same and each represents OY or —A—$(CH_2)$n-E. n represents a whole number of 0–4. E represents pyrrolidino, piperidino, substituted or unsubstituted piperazino, morpholino, substituted or unsubstituted guanidino, or

($R^3$ and $R^4$ are the same or different and each represents hydrogen, lower($C_{1-4}$) alkyl, hydroxy-lower($C_{1-4}$) alkyl, or mono- or di-(lower) alkylaminoalkyl($C_{2-6}$)). A represents the followings ①, ②, ③, ④, ⑤ ⑥ or ⑦.

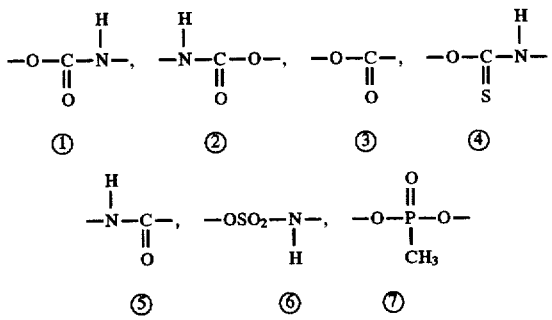

R and Y are the same or different and each represents a saturated or unsaturated aliphatic hydrocarbon group of 10–30 carbon atoms or a saturated or unsaturated fatty acid residue of 10–30 carbon atoms.

The substituted piperazino for E includes 4-methylpiperazino, 4-ethylpiperazino, 4-n-propylpiperazino, 4-isopropylpiperazino, 4-n-butylpiperazino, 4-isobutylpiperazino, 4-(2-hydroxyethyl)piperazino, 4-(2-hydroxypropyl)piperazino, and 4-(3-hydroxypropyl)piperazino, among others.

The substituted guanidino for E includes methylguanidino, ethylguanidino, n-propylguanidino, N,N-dimethylguanidino, N,N-diethylguanidino, N,N-di-n-propylguanidino, N,N'-dimethylguanidino, N,N'-diethylguanidino, N,N'-di-n-propylguanidino, N,N,N'-trimethylguanidino, N,N,N'-triethylguanidino, N,N,N'-tri-n-propylguanidino, N,N,N',N'-tetramethylguanidino, N,N,N',N'-tetraethylguanidino, and N,N,N',N'-tetra-n-propylguanidino, among others.

The lower alkyl for $R^3$ and $R^4$ includes methyl, ethyl, n-propyl, isopropyl, n-butyl, isobutyl, sec-butyl, and tert-butyl, among others.

The hydroxy(lower)alkyl for and $R^3$ and $R^4$ includes hydroxymethyl, 1-hydroxyethyl, 2-hydroxyethyl, 1-hydroxypropyl, 2-hydroxypropyl, and 3-hydroxypropyl, among others.

The mono- or di-(lower)alkylaminoalkyl for $R^3$ and $R^4$ includes methylaminomethyl, dimethylaminomethyl, 2-(methylamino)ethyl, 2-dimethylaminoethyl, 3-(methylamino)propyl, 3-dimethylaminopropyl, ethylaminomethyl, diethylaminomethyl, 2-(ethylamino)ethyl, 2-diethylaminoethyl, 3-(ethylamino)propyl, 3-diethylaminopropyl, n-propylaminomethyl, di-n-propylaminomethyl, 2-(n-propylamino)ethyl, 2-(di-n-propylamino)ethyl, 3-(n-propylamino)propyl, and 3-(di-n-propylamino)propyl, among others.

Referring further to general formula [I], R and Y are the same or different and each represents a saturated or unsaturated aliphatic hydrocarbon group of 10–30 carbon atoms or a saturated or unsaturated fatty acid residue of 10–30 carbon atoms as mentioned above. However, the preferred is the case in which R and Y are the same and each represents an unsaturated aliphatic hydrocarbon or unsaturated fatty acid residue of about 12–20 carbon atoms. The most preferred is the case in which both R and Y represent oleyl or oleoyl, for instance.

A is preferably a carbamate bond or an ester bond.

Specifically, the following compounds can be mentioned as typical examples.

3-O-(2-Dimethylaminoethyl)carbamoyl-1,2-O-dilaurylglycerol,
3-O-(2-Dimethylaminoethyl)carbamoyl-1,2-O-dimyristylglycerol,
3-O-(2-Dimethylaminoethyl)carbamoyl-1,2-O-dipalmitylglycerol,
3-O-(2-Dimethylaminoethyl)carbamoyl-1,2-O-dioleylglycerol,
3-O-(2-Dimethylaminoethyl)carbamoyl-1,2-O-dilinoleylglycerole,
3-O-(2-Dimethylaminoethyl)carbamoyl-2-O-lauryl-1-O-myristylglycerol,
3-O-(2-Dimethylaminoethyl)carbamoyl-1-O-oleyl-2-O-palmitylglycerol,
3-O-(2-Dimethylaminoethyl)carbamoyl-1-O-linoleyl-2-O-oleylglycerol,
3-O-(Dimethylaminomethyl)carbamoyl-1,2-O-dioleylglycerol,
3-O-(3-Dimethylaminopropyl)carbamoyl-1,2-O-dioleylglycerol,
3-O-(4-Dimethylaminobutyl)carbamoyl-1,2-O-dioleylglycerol,
3-O-(2-Diethylaminoethyl)carbamoyl-1,2-O-dioleylglycerol,
3-O-(3-Diethylaminopropyl)carbamoyl-1,2-O-dioleylglycerol,
3-O-(2-Di-n-propylaminoethyl)carbamoyl-1,2-O-dioleylglycerol,
3-O-(2-Diisopropylaminoethyl)carbamoyl-1,2-O-dioleylglycerol,
3-O-(2-Di-n-butylaminoethyl)carbamoyl-1,2-O-dioleylglycerol,
3-O-(2-Diisobutylaminoethyl)carbamoyl-1,2-O-dioleylglycerol,
3-O-(2-Di-sec-butylaminoethyl)carbamoyl-1,2-O-dioleylglycerol,
3-O-[2-(N-Ethyl-N-methylamino)ethyl]carbamoyl-1,2-O-dioleylglycerol,
3-O-(2-Methylaminoethyl)carbamoyl-1,2-O-dioleylglycerol,
3-O-(2-Ethylaminoethyl)carbamoyl-1,2-O-dioleylglycerol,
3-O-(2-n-Propylaminoethyl)carbamoyl-1,2-O-dioleylglycerol,
3-O-(2-n-Butylaminoethyl)carbamoyl-1,2-O-dioleylglycerol,
3-O-(2-Aminoethyl)carbamoyl-1,2-O-dioleylglycerol,
3-O-[2-(N-Methyl-N-(2-hydroxyethyl)amino)ethyl]carbamoyl-1,2-O-dioleylglycerol,
3-O-[2-(N-Ethyl-N-(2-hydroxyethyl)amino)ethyl]carbamoyl-1,2-O-dioleylglycerol,
3-O-[2-(N,N-Di-(2-hydroxyethyl)amino)ethyl]carbamoyl-1,2-O-dioleylglycerol,
3-O-[2-(N-(2-Diethylamino)ethyl-N-methylamino)ethyl]carbamoyl-1,2-O-dioleylglycerol,
3-O-[2-(4-Methylpiperazino)ethyl]carbamoyl-1,2-O-dioleylglycerol,
3-O-(2-Morpholinoethyl)carbamoyl-1,2-O-dioleylglycerol,
3-O-(2-Piperidinoethyl)carbamoyl-1,2-O-dioleylglycerol,
3-O-(2-Pyrrolidinoethyl)carbamoyl-1,2-O-dioleylglycerol,
3-O-(2-Diethylaminoethyl)thiocarbamoyl-1,2-O-dioleylglycerol,
3-O-(2-Dimethylaminoethyl)thiocarbamoyl-1,2-O-dioleylglycerol,
3-O-[2-(N,N-Di-(2-hydroxyethyl)amino)ethyl]thiocarbamoyl-1,2-O-dioleylglycerol,
3-O-(2-Pyrrolidinoethyl)thiocarbamoyl-1,2-O-dioleylglycerol,
3-O-(2-Dimethylaminoethyl)sulfamoyl-1,2-O-dioleylglycerol,
3-O-(2-Diethylaminoethyl)sulfamoyl-1,2-O-dioleylglycerol,
3-O-[2-N,N-Di-(2-hydroxyethyl)amino)ethyl]sulfamoyl-1,2-O-dioleylglycerol,
3-O-(2-Pyrrolidinoethyl)sulfamoyl-1,2-O-dioleylglycerol,
3-O-(N,N-Dimethylaminoacetyl)-1,2-O-dioleylglycerol,
3-O-(4-Dimethylaminobutanoyl)-1,2-O-dilaurylglycerol,
3-O-(4-Diethylaminobutanoyl)-1,2-O-dipalmitylglycerol,
3-O-(4-diemthylaminobutanoyl)-1,2-O-dioleylglycerol,
3-O-(4-Diethylaminobutanoyl)-1,2-O-dioleylglycerol,
3-O-(4-Dimethylaminobutanoyl)-1,2-O-dilinoleylglycerol,
3-O-(4-Dimethylaminobutanoyl)-1-O-oleyl-2-O-palmitylglycerol,
3-O-(4-Dimethylaminobutanoyl)-1-O-linoleyl-2-O-oleylglycerol,
3-O-(3-Dimethylaminopropionyl)-1,2-O-dioleylglycerol,
3-O-(5-Dimethylaminopentanoyl)-1,2-O-dioleylglycerol,
3-O-(4-Di-n-propylaminobutanoyl)-1,2-O-dioleylglycerol,
3-O-(4-Diisopropylaminobutanoyl)-1,2-O-dioleylglycerol,
3-O-[4-(N-Ethyl-N-methylamino)butanoyl]-1,2-O-dioleylglycerol,
3-O-[4-Ethylaminobutanoyl)-1,2-O-dioleylglycerol,
3-O-[4-(N-Methyl-N-(2-hydroxyethyl)amino)butanoyl]-1,2-O-dioleylglycerol,
3-O-[4-(N,N-Di-(2-hydroxyethyl)amino)butanoyl]-1,2-O-dioleylglycerol,
3-O-[4-(N-(2-Diethylamino)ethyl-N-methylamino)butanoyl]-1,2-O-dioleylglycerol,
3-O-[4-(4-Methylpiperazino)butanoyl]-1,2-O-dioleylglycerol,
3-O-(4-Morpholinobutanoyl)-1,2-O-dioleylglycerol,
3-O-(4-Pyrrolidinobutanoyl)-1,2-O-dioleylglycerol,
3-O-(4-Piperidinobutanoyl)-1,2-O-dioleylglycerol,
O-(2-Diethylaminoethyl)-O'-(2,3-dioleyloxypropyl)methylphosphonate,
O-(2-Dimethylaminoethyl)-O'-(2,3-dioleyloxypropyl)methylphosphonate,
O-[2-(N,N-di(2-hydroxyethyl)amino)ethyl]-O'-(2,3-dioleyloxypropyl)methylphosphonate,
O-(2-Pyrrolidinoethyl)-O'-(2,3-dioleyloxypropyl)methylphosphonate,
3-O-(2-Dimethylaminoethyl)carbamoyl-1,2-O-dilauroylglycerol,
3-O-(2-Dimethylaminoethyl)carbamoyl-1,2-O-dimyristoylglycerol,
3-O-(2-Dimethylaminoethyl)carbamoyl-1,2-O-dipalmitoylglycerol,
3-O-(2-Dimethylaminoethyl)carbamoyl-1,2-O-dioleoylglycerol,
3-O-(2-Dimethylaminoethyl)carbamoyl-1,2-O-dilinolenylglycerol,
3-O-(2-Dimethylaminoethyl)carbamoyl-1-O-oleoyl-2-O-palmitoylglycerol,
3-O-(2-Dimethylaminoethyl)carbamoyl-1-O-linolenyl-2-O-oleoylglycerol,
3-O-(3-Dimethylaminopropyl)carbamoyl-1,2-O-dioleoylglycerol, 3-O-(2-Diethylaminoethyl)carbamoyl-1,2-O-dioleoylglycerol,
3-O-(2-Di-n-propylaminoethyl)carbamoyl-1,2-O-dioleoylglycerol,
3-O-(2-Diisopropylaminoethyl)carbamoyl-1,2-O-dioleoylglycerol,
3-O-[2-(N-Ethyl-N-methylamino)ethyl]carbamoyl-1,2-O-dioleoylglycerol,
3-O-(2-Ethylaminoethyl)carbamoyl-1,2-O-dioleoylglycerol,
3-O-[2-(N-Methyl-N-(2-hydroxyethyl)amino)ethyl]carbamoyl-1,2-O-dioleoylglycerol,
3-O-[2-(N,N-Di-(2-hydroxyethyl)amino)ethyl]carbamoyl-1,2-O-dioleoylglycerol,
3-O-[2-(N-(2-Diethylamino)ethyl-N-methylamino)ethyl]carbamoyl-1,2-O-dioleoylglycerol,
3-O-(2-Piperidinoethyl)carbamoyl-1,2-O-dioleoylglycerol,
3-O-(2-Pyrrolidinoethyl)carbamoyl-1,2-O-dioleoylglycerol,
3-O-(2-Aminoethyl)carbamoyl-1,2-O-dioleoylglycerol
3-O-(2-Diethylaminoethyl)thiocarbamoyl-1,2-O-dioleoylglycerol,
3-O-(2-Dimethylaminoethyl)thiocarbamoyl-1,2-O-dioleoylglycerol,
3-O-[2-(N,N-Di-(2-hydroxyethyl)amino)ethyl]thiocarbamoyl-1,2-O-dioleoylglycerol,
3-O-(2-Pyrrolidinoethyl)thiocarbamoyl-1,2-O-dioleoylglycerol,
3-O-(2-Diethylaminoethyl)sulfamoyl-1,2-O-dioleoylglycerol,
3-O-(2-Dimethylaminoethyl)sulfamoyl-1,2-O-dioleoylglycerol,
3-O-[2-(N,N-Di-(2-hydroxyethyl)amino)ethyl]sulfamoyl-1,2-O-dioleoylglycerol,
3-O-(2-Pyrrolidinoethyl)sulfamoyl-1,2-O-dioleoylglycerol,
3-O-(4-Dimethylaminobutanoyl)-1,2-O-dilauroylglycerol,
3-O-(4-Dimethylaminobutanoyl)-1,2-O-dimyristoylglycerol,
3-O-(4-Dimethylaminobutanoyl)-1,2-O-dipalmitoylglycerol,
3-O-(4-Dimethylaminobutanoyl)-1,2-O-dioleoylglycerol,
3-O-(4-Dimethylaminobutanoyl)-1,2-O-dilinolenylglycerol,
3-O-(4-Dimethylaminobutanoyl)-1-O-oleoyl-2-O-palmitoylglycerol,
3-O-(4-Dimethylaminobutanoyl)-1-O-linolenyl-2-O-oleoylglycerol,
3-O-(3-Dimethylaminopropionyl)-1,2-O-dioleoylglycerol,
3-O-(5-Dimethylaminopentanoyl)-1,2-O-dioleoylglycerol,
3-O-(4-Diethylaminobutanoyl)-1,2-O-dioleoylglycerol,
3-O-(4-Di-n-propylaminobutanoyl)-1,2-O-dioleoylglycerol,
3-O-(4-Diisopropylaminobutanoyl)-1,2-O-dioleoylglycerol,
3-O-[4-(N-Ethyl-N-methylamino)butanoyl]-1,2-O-dioleoylglycerol,
3-O-(4-Ethylaminobutanoyl)-1,2-O-dioleoylglycerol,
3-O-[4-(N-Methyl-N-(2-hydroxyethyl)amino)butanoyl]-1,2-O-dioleoylglycerol,
3-O-[4-(N,N-Di-(2-hydroxyethyl)amino)butanoyl]-1,2-O-dioleoylglycerol,
3-O-[4-(N-(2-Diethylamino)ethyl-N-methylamino)butanoyl]-1,2-O-dioleoylglycerol
3-O-(4-Pyrrolidinobutanoyl)-1,2-O-dioleoylglycerol,
O-(2-Diethylaminoethyl)-O'-(2,3-dioleoyloxypropyl)methylphosphonate,
O-(2-Dimethylaminoethyl)-O'-(2,3-dioleoyloxypropyl)methylphosphonate,
O-[2-(N,N-Di-(2-hydroxyethyl)amino)ethyl]-O'-(2,3-dioleoyloxypropyl)methylphosphonate,
O-(2-Pyrrolidinoethyl)-O'-(2,3-dioleoyloxypropyl)methylphosphonate,
2-O-(2-Dimethylaminoethyl)carbamoyl-1,3-O-dilaurylglycerol,
2-O-(2-Dimethylaminoethyl)carbamoyl-1,3-O-dimyristylglycerol,
2-O-(2-Dimethylaminoethyl)carbamoyl-1,3-O-dipalmitylglycerol,
2-O-(2-Dimethylaminoethyl)carbamoyl-1,3-O-dioleylglycerol,
2-O-(2-Dimethylaminoethyl)carbamoyl-1,3-O-dilinoleylglycerol,
2-O-(2-Dimethylaminoethyl)carbamoyl-1-O-lauryl-3-O-myristylglycerol,
2-O-(2-Dimethylaminoethyl)carbamoyl-1-O-oleyl-3-O-palmitylglycerol,
2-O-(2-Dimethylaminoethyl)carbamoyl-1-O-linoleyl-3-O-oleylglycerol,
2-O-(3-Dimethylaminopropyl)carbamoyl-1,3-O-dioleylglycerol,
2-O-(4-Dimethylaminobutyl)carbamoyl-1,3-O-dioleylglycerol,
2-O-(2-Diethylaminoethyl)carbamoyl-1,3-O-dioleylglycerol,
2-O-(2-Di-n-propylaminoethyl)carbamoyl-1,3-O-dioleylglycerol,
2-O-(2-diisopropylaminoethyl)carbamoyl-1,3-O-dioleylglycerol,
2-O-(2-Di-n-butylaminoethyl)carbamoyl-1,3-O-dioleylglycerol,
2-O-(2-Diisobutylaminoethyl)carbamoyl-,3-O-dioleylglycerol,
2-O-(2-Di-sec-butylaminoethyl)carbamoyl-1,3-O-dioleylglycerol,
2-O-[2-(N-Ethyl-N-methyl)aminoethyl]carbamoyl-1,3-O-dioleylglycerol,
2-O-(2-Methylaminoethyl)carbamoyl-1,3-O-dioleylglycerol,
2-O-(2-Ethylaminoethyl)carbamoyl-1,3-O-dioleylglycerol,
2-O-(2-n-Propylaminoethyl)carbamoyl-1,3-O-dioleylglycerol,
2-O-(2-Butylaminoethyl)carbamoyl-1,3-O-dioleylglycerol,
2-O-(2-Aminoethyl)carbamoyl-1,3-O-dioleylglycerol,
2-O-[2-(N-Methyl-N-(2-hydroxyethyl)amino)ethyl]carbamoyl-1,3-O-dioleylglycerol,
2-O-[2-(N-Ethyl-N-(2-hydroxyethyl)amino)ethyl]carbamoyl-1,3-O-dioleylglycerol,
2-O-[2-(N,N-Di-(2-hydroxyethyl)amino)ethyl]carbamoyl-1,3-O-dioleylglycerol,
2-O-[2-(N-(2-Diethylamino)ethyl-N-methylamino)ethyl]carbamoyl-1,3-O-dioleylglycerol,
2-O-[2-(4-Methylpiperazino)ethyl]carbamoyl-1,3-O-dioleylglycerol,
2-O-(2-Morpholinoethyl)carbamoyl-1,3-O-dioleylglycerol,
2-O-(2-Piperidinoethyl)carbamoyl-1,3-O-dioleylglycerol,
2-O-(2-Pyrrolidinoethyl)carbamoyl-1,3-O-dioleylglycerol,
2-O-(2-Dimethylaminoethyl)thiocarbamoyl-1,3-O-dioleylglycerol,
2-O-(2-Diethylaminoethyl)thiocarbamoyl-1,3-O-dioleylglycerol,
2-O-[2-(N,N-Di-(2-hydroxyethyl)amino)ethyl]thiocarbamoyl-1,3-O-dioleylglycerol,
2-O-(2-Pyrrolidinoethyl)thiocarbamoyl-1,3-O-dioleylglycerol,
2-O-(2-Dimethylaminoethyl)sulfamoyl-1,3-O-dioleylglycerol,
2-O-(2-Diethylaminoethyl)sulfamoyl-1,3-O-dioleylglycerol,
2-O-[2-(N,N-Di-(2-hydroxyethyl)amino)ethyl]sulfamoyl-1,3-O-dioleylglycerol, 2-O-(2-Pyrrolidinoethyl)sulfamoyl-1,3-O-dioleylglycerol,
2-O-(4-Dimethylaminobutanoyl)-1,3-O-dilaurylglycerol,
2-O-(4-Diethylaminobutanoyl)-1,3-O-dipalmitylglycerol,
2-O-(4-Dimethylaminobutanoyl)-1,3-O-dilinoleylglycerol,
2-O-(4-Dimethylaminobutanoyl)-1-O-oleyl-3-O-palmitylglycerol,
2-O-(4-Dimethylaminobutanoyl)-1-O-linoleyl-3-O-oleylglycerol,
2-O-(3-Dimethylaminopropionyl)-1,3-O-dioleylglycerol,
2-O-(5-Dimethylaminopentanoyl)-1,3-O-dioleylglycerol,
2-O-(4-Di-n-propylaminobutanoyl)-1,3-O-dioleylglycerol,
2-O-(4-Diisopropylaminobutanoyl)-1,3-O-dioleylglycerol,
2-O-[4-(N-Ethyl-N-methyl)aminobutanoyl]-1,3-O-dioleylglycerol,
2-O-(4-Ethylaminobutanoyl)-1,3-O-dioleylglycerol,
2-O-[4-(N-Methyl-N-(2-hydroxyethyl)amino)butanoyl]-1,3-O-dioleylglycerol,
2-O-[4-(N,N-Di-(2-hydroxyethyl)amino)butanoyl]-1,3-O-dioleylglycerol,
2-O-[4-(N-(2-Diethylamino)ethyl-N-methylamino)butanoyl]-1,3-O-dioleylglycerol,
2-O-[4-(4-Methylpiperazino)butanoyl]-1,3-O-dioleylglycerol,
2-O-(4-Morpholinobutanoyl)-1,3-O-dioleylglycerol,
2-O-(4-Pyrrolidinobutanoyl)-1,3-O-dioleylglycerol,
2-O-(4-Piperidinobutanoyl)-1,3-O-dioleylglycerol,
O-(2-Diethylaminoethyl)-O'-(1,3-dioleyloxypropyl)methylphosphonate,
O-(2-Dimethylaminoethyl)-O'-(1,3-dioleyloxypropan-2-yl)methylphosphonate,
O-[2-(N,N-Di-(2-hydroxyethyl)amino)ethyl]-O'-(1,3-dioleyloxypropan-2-yl)methylphosphonate,
O-(2-Pyrrolidinoethyl)-O'-(1,3-dioleyloxypropan-2-yl)methylphosphonate,
2-O-(2-Dimethylaminoethyl)carbamoyl-1,3-O-dilauroylglycerol,
2-O-(2-Dimethylaminoethyl)carbamoyl-1,3-O-dimyristoylglycerol,
2-O-(2-Dimethylaminoethyl)carbamoyl-1,3-O-dipalmitoylglycerol,
2-O-(2-Diethylaminoethyl)carbamoyl-1,3-O-dipalmitoylglycerol,
2-O-(2-Dimethylaminoethyl)carbamoyl-1,3-O-dioleoylglycerol,
2-O-(2-Dimethylaminoethyl)carbamoyl-1,3-O-dilinolenylglycerol,
2-O-(2-Dimethylaminoethyl)carbamoyl-1-O-oleoyl-3-O-palmitoylglycerol,
2-O-(2-Dimethylaminoethyl)carbamoyl-1-O-linolenyl-3-O-oleoylglycerol,
2-O-(Dimethylaminomethyl)carbamoyl-1,3-O-dioleoylglycerol,
2-O-(3-Dimethylaminopropyl)carbamoyl-1,3-O-dioleoylglycerol,
2-O-(2-Diethylaminoethyl)carbamoyl-1,3-O-dioleoylglycerol,
2-O-(2-Di-n-propylaminoethyl)carbamoyl-1,3-O-dioleoylglycerol,
2-O-(2-Diisopropylaminoethyl)carbamoyl-1,3-O-dioleoylglycerol,
2-O-[2-(N-Ethyl-N-methylamino)ethyl]carbamoyl-1,3-O-dioleoylglycerol,
2-O-[2-(N-Methyl-N-n-butylamino)ethyl]carbamoyl-1,3-O-dioleoylglycerol,
2-O-(2-Ethylaminoethyl)carbamoyl-1,3-O-dioleoylglycerol,
2-O-[2-(N,N-Di-(2-hydroxyethyl)amino)ethyl]carbamoyl-1,3-O-dioleoylglycerol,
2-O-[2-(N-Methyl-N-(2-hydroxyethyl)amino)ethyl]carbamoyl-1,3-O-dioleoylglycerol,
2-O-[2-(N-Ethyl-N-(2-hydroxyethyl)amino)ethyl]carbamoyl-1,3-O-dioleoylglycerol,
2-O-[2-(N-(2-Diethylamino)ethyl-N-methylamino)ethyl]carbamoyl-1,3-O-dioleoylglycerol,
2-O-[2-(N,N,N',N'-Tetramethylguanidino)ethyl]carbamoyl-1,3-O-dioleoylglycerol,
2-O-(2-Morpholinoethyl)carbamoyl-1,3-O-dioleoylglycerol,
2-O-(2-Piperidinoethyl)carbamoyl-1,3-O-dioleoylglycerol,
2-O-(2-Pyrrolidinoethyl)carbamoyl-1,3-O-dioleoylglycerol,
2-O-[2-(4-Ethylpiperazino)ethyl]carbamoyl-1,3-O-dioleoylglycerol,
2-O-[2-(4-(2-Hydroxyethyl)piperazino)ethyl]carbamoyl-1,3-O-dioleoylglycerol,
2-O-(2-Diethylaminoethyl)thiocarbamoyl-1,3-O-dioleoylglycerol,
2-O-(2-Dimethylaminoethyl)thiocarbamoyl-1,3-O-dioleoylglycerol,
2-O-[2-(N,N-Di-(2-hydroxyethyl)amino)ethyl]thiocarbamoyl-1,3-O-dioleoylglycerol,
2-O-(2-Pyrrolidinoethyl)thiocarbamoyl-1,3-O-dioleoylglycerol,
2-O-(2-Diethylaminoethyl)sulfamoyl-1,3-O-dioleoylglycerol,
2-O-(2-Dimethylaminoethyl)sulfamoyl-1,3-O-dioleoylglycerol,
2-O-[2-N,N-Di-(2-hydroxyethyl)aminoethyl]sulfamoyl-1,3-O-dioleoylglycerol,
2-O-(2-Pyrrolidinoethyl)sulfamoyl-1,3-O-dioleoylglycerol,
2-O-(3-Diethylaminopropionyl)-1,3-O-dioleoylglycerol,
2-O-(4-Dimethylaminobutanoyl)-1,3-O-dilauroylglycerol,
2-O-(4-Dimethylaminobutanoyl)-1,3-O-dimyristoylglycerol,
2-O-(4-Dimethylaminobutanoyl)-1,3-O-dipalmitoylglycerol,
2-O-(4-Dimethylaminobutanoyl)-1,3-O-dioleoylglycerol,
2-O-(4-Dimethylaminobutanoyl)-1,3-O-dilinolenylglycerol,
2-O-(4-Dimethylaminobutanoyl)-1-O-oleoyl-3-O-palmitoylglycerol,
2-O-(4-Dimethylaminobutanoyl)-1-O-linolenyl-3-O-oleoylglycerol,
2-O-(3-Dimethylaminopropionyl)-1,3-O-dioleoylglycerol,
2-O-(5-Dimethylaminopentanoyl)-1,3-O-dioleoylglycerol,
2-O-(4-Diethylaminobutanoyl)-1,3-O-dioleoylglycerol,
2-O-(4-Di-n-propylaminobutanoyl)-1,3-O-dioleoylglycerol,
2-O-(4-Diisopropylaminobutanoyl)-1,3-O-dioleoylglycerol,
2-O-[4-(N-Ethyl-N-methylamino)butanoyl]-1,3-O-dioleoylglycerol,
2-O-[4-(Ethyl)aminobutanoyl]-1,3-O-dioleoylglycerol,
2-O-[4-(N-Methyl-N-(2-hydroxyethyl)amino)butanoyl]-1,3-O-dioleoylglycerol,
2-O-[4-(N,N-Di-(2-hydroxyethyl)amino)butanoyl]-1,3-O-dioleoylglycerol,
2-O-[4-(N-(2-Diethylamino)ethyl-N-methylamino)butanoyl]-1,3-O-dioleoylglycerol,
2-O-(4-Pyrrolidinobutanoyl)-1,3-O-dioleoylglycerol,
O-(2-Dimethylaminoethyl)-O'-(1,3-dioleoyloxypropan-2-yl)methylphosphonate,
O-(2-Aminoethyl)-O'-(1,3-dioleoyloxypropan-2-yl)methylphosphonate,
O-(2-Diethylaminoethyl)-O'-(1,3-dioleoyloxypropan-2-yl)methylphosphonate,
2-Dimethylaminoethyl N-(2,3-dilauryloxypropyl)carbamate,
2-Dimethylaminoethyl N-(2,3-dimyristyloxypropyl)carbamate, 2-Dimethylaminoethyl N-(2,3-dioleyloxypropyl)carbamate,
2-Dimethylaminoethyl N-(2,3-dilinoleyloxypropyl) carbamate,
2-Dimethylaminoethyl N-(2-lauryloxy-3-linoleyloxypropyl)carbamate,
2-Dimethylaminoethyl N-(3-myristyloxy-2-oleyloxypropyl) carbamate,
3-Dimethylaminopropyl N-(2,3-dioleyloxypropyl) carbamate,
4-Dimethylaminobutyl N-(2,3-dioleyloxypropyl)carbamate,
2-Diethylaminoethyl N-(2,3-dioleyloxypropyl)carbamate,
2-Di-n-propylaminoethyl N-(2,3-dioleyloxypropyl) carbamate,
2-Di-n-butylaminoethyl N-(2,3-dioleyloxypropyl) carbamate,
2-Ethylmethylaminoethyl N-(2,3-dioleyloxypropyl) carbamate,
2-(N-Ethyl-N-methylamino)ethyl N-(2,3-dioleyloxypropyl) carbamate,
2-Ethylaminobutyl N-(2,3-dioleyloxypropyl)carbamate,
2-n-Propylaminoethyl N-(2,3-dioleyloxypropyl)carbamate,
2-[N-Methyl-N-(2-hydroxyethyl)amino]ethyl N-(2,3-dioleyloxypropyl)carbamate,
2-[N-Ethyl-N-(2-hydroxyethyl)amino]ethyl N-(2,3-dioleyloxypropyl)carbamate,
2-[N,N-Di-(2-hydroxyethyl)amino]ethyl N-(2,3-dioleyloxypropyl)carbamate,
2-[N-(2-Diethylamino)ethyl-N-methylamino]ethyl N-(2,3-dioleyloxypropyl)carbamate,
2-(4-Methylpiperadino)ethyl N-(2,3-dioleyloxypropyl) carbamate,
2-Morpholinoethyl N-(2,3-dioleyloxypropyl)carbamate,
2-Piperidinoethyl N-(2,3-dioleyloxypropyl)carbamate,
2-Pyrrolidinoethyl N-(2,3-dioleyloxypropyl)carbamate,
2-Dimethylaminoethyl N-(2,3-dioleyloxypropyl) thiocarbamate,
2-Diethylaminoethyl N-(2,3-dioleyloxypropyl) thiocarbamate,
2-[N,N-Di-(2-hydroxyethyl)amino]ethyl N-(2,3-dioleyloxypropyl)thiocarbamate,
2-Pyrrolidinoethyl N-(2,3-dioleyloxypropyl)thiocarbamate,
2-Dimethylaminoethyl N-(2,3-dioleyloxypropyl)sulfamate,
2-Diethylaminoethyl N-(2,3-dioleyloxypropyl)sulfamate,
2-[N,N-Di-(2-hydroxyethyl)amino]ethyl N-(2,3-dioleyloxypropyl)sulfamate,
2-Pyrrolidinoethyl N-(2,3-dioleyloxypropyl)sulfamate,
N-(2,3-Dioleyloxy)propyl-4-dimethylaminobutylamide,
N-(2,3'Dioleyloxy)propyl-4-diethylaminobutylamide,
N-(2,3'Dioleyloxy)propyl-4-[N,N-di(2-hydroxyethyl)amino]butylamide,
N-(2,3'Dioleyloxy)propyl-4-pyrrolidinobutylamide,
2-Dimethylaminoethyl N-(2,3-dilauroyloxypropyl) carbamate,
2-Dimethylaminoethyl N-(2,3-dimyristoyloxypropyl) carbamate,
2-Dimethylaminoethyl N-(2,3-dipalmitoyloxypropyl) carbamate,
2-Dimethylaminoethyl N-(2,3-dioleoyloxypropyl) carbamate,
2-Dimethylaminoethyl N-(2,3-dilinolenyloxypropyl) carbamate,
2-Dimethylaminoethyl N-(2-oleoyloxy-3-palmitoyloxypropyl)carbamate,
2-Dimethylaminoethyl N-(2-linolenyloxy-3-oleoyloxypropyl)carbamate,
2-Diethylaminoethyl N-(2,3-dioleoyloxypropyl)carbamate,
3-Dimethylaminopropyl N-(2,3-dioleoyloxypropyl) carbamate,
2-Diisopropylaminoethyl N-(2,3-dioleoyloxypropyl) carbamate,
2-Di-n-propylaminoethyl N-(2,3-dioleoyloxypropyl) carbamate,
2-(N-Ethyl-N-methylamino)ethyl N-(2,3-dioleoyloxypropyl)carbamate,
2-Ethylaminoethyl N-(2,3-dioleoyloxypropyl)carbamate,
2-[N-methyl-N-(2-hydroxyethyl)amino]ethyl N-(2,3-dioleoyloxypropyl)carbamate,
2-[N,N-Di-(2hydroxyethyl)amino]ethyl N-(2,3-dioleoyloxypropyl)carbamate,
2-[N-(2-Diethylamino)ethyl-N-methylamino]ethyl N-(2,3-dioleoyloxypropyl)carbamate,
2-Piperidinoethyl N-(2,3-dioleoyloxypropyl)carbamate,
2-Pyrrolidinoethyl N-(2,3-dioleoyloxypropyl)carbamate,
2-Aminoethyl N-(2,3-dioleoyloxypropyl)carbamate,
2-Dimethylaminoethyl N-(2,3-dioleoyloxypropyl) thiocarbamate,
2-Diethylaminoethyl N-(2,3-dioleoyloxypropyl) thiocarbamate,
2-[N,N-Di-(2-hydroxyethyl)aminoethyl] N-(2,3-dioleoyloxypropyl)thiocarbamate,
2-Pyrrolidinoethyl N-(2,3-dioleoyloxypropyl) thiocarbamate,
2-Dimethylaminoethyl N-(2,3-dioleoyloxypropyl) sulfamate,
2-Diethylaminoethyl N-(2,3-dioleoyloxypropyl)sulfamate,
2-[N,N-Di-(2-hydroxyethyl)aminoethyl] N-(2,3-dioleoyloxypropyl)sulfamate,
2-Pyrrolidinoethyl N-(2,3-dioleoyloxypropyl)sulfamate,
N-(2,3-Dioleoyloxy)propyl-4-dimethylaminobutylamide,
N-(2,3-Dioleoyloxy)propyl-4-diethylaminobutylamide,
N-(2,3-Dioleoyloxy)propyl-4-[N,N-di-(2-hydroxyethyl)amino]butylamide,
N-(2,3-Dioleoyloxy)propyl-4-pyrrolidinobutylamide,
2-Dimethylaminoethyl N-(1,3-dilauryloxypropan-2-yl) carbamate,
2-Dimethylaminoethyl N-(1,3-dimyristyloxypropan-2-yl) carbamate,
2-Dimethylaminoethyl N-(1,3-dioleyloxypropan-2-yl) carbamate,
2-Dimethylaminoethyl N-(1,3-dilinoleyloxypropan-2-yl) carbamate,
2-Dimethylaminoethyl N-(1-lauryloxy-3-linoleyloxypropan-2-yl)carbamate,
2-Dimethylaminoethyl N-(1-myristyloxy-3-oleyloxypropan-2-yl)carbamate,
2-Dimethylaminoethyl N-(1-oleyloxy-3-palmityloxypropan-2-yl)carbamate,
3-Dimethylaminopropyl N-(1,3-dioleyloxypropan-2-yl) carbamate,
4-Dimethylaminobutyl N-(1,3-dioleyloxypropan-2-yl) carbamate,
2-Diethylaminoethyl N-(1,3-dioleyloxypropan-2-yl) carbamate,
2-Di-n-propylaminoethyl N-(1,3-dioleyloxypropan-2-yl) carbamate,
2-Di-n-butylaminoethyl N-(1,3-dioleyloxypropan-2-yl) carbamate,
2-(N-Ethyl-N-methylamino)ethyl N-(1,3-dioleyloxypropan-2-yl)carbamate,
2-Methylaminoethyl N-(1,3-dioleyloxypropan-2-yl) carbamate,
2-Ethylaminobutyl N-(1,3-dioleyloxypropan-2-yl) carbamate,
2-n-Propylaminoethyl N-(1,3-dioleyloxypropan-2-yl) carbamate, 2-n-Butylamino N-(1,3-dioleyloxypropan-2-yl)carbamate,
2-[N-Methyl-N-(2-hydroxyethyl)amino]ethyl N-(1,3-dioleyloxypropan-2-yl)carbamate,
2-[N-Ethyl-N-(2-hydroxyethyl)amino]ethyl N-(1,3-dioleyloxypropan-2-yl)carbamate,
2-[N,N-Di-(2-hydroxyethyl)amino]ethyl N-(1,3-dioleyloxypropan-2-yl)carbamate,
2-[N-(2-Diethylamino)ethyl-N-methylamino]ethyl N-(1,3-dioleyloxypropan-2-yl)carbamate,
2-(4-Methylpiperadino)ethyl N-(1,3-dioleyloxypropan-2-yl)carbamate,
2-Piperidinoethyl N-(1,3-dioleyloxypropan-2-yl)carbamate,
2-Pyrrolidinoethyl N-(1,3-dioleyloxypropan-2-yl)carbamate,
2-Dimethylaminoethyl N-(1,3-dioleyloxypropan-2-yl)thiocarbamate,
2-Diethylaminoethyl N-(1,3-dioleyloxypropan-2-yl)thiocarbamate,
2-[N,N-Di-(2-hydroxyethyl)amino]ethyl N-(1,3-dioleyloxypropan-2-yl)thiocarbamate,
2-Pyrrolidinoethyl N-(1,3-dioleyloxypropan-2-yl)thiocarbamate,
2-Dimethylaminoethyl N-(1,3-dioleyloxypropan-2-yl)sulfamate,
2-Diethylaminoethyl N-(1,3-dioleyloxypropan-2-yl)sulfamate,
2-[N,N-Di-(2-hydroxyethyl)amino]ethyl N-(1,3-dioleyloxypropan-2-yl)sulfamate,
2-Pyrrolidinoethyl N-(1,3-Dioleyloxypropan-2-yl)sulfamate,
N-(4-Dimethylaminobutanoyl)-1,3-dioleyloxy-1-aminopropane,
N-(4-Diethylaminobutanoyl)-1,3-dioleyloxy-1-aminopropane,
N-[4-(N,N-Di-(2-hydroxyethyl)amino)butanoyl]-1,3-dioleyloxy-1-amino-propane,
N-4-Pyrrolidinobutanoyl-1,3-dioleyloxy-1-amino-propane,
2-Dimethylaminoethyl N-(1,3-dilauroyloxypropan-2-yl)carbamate,
2-Dimethylaminoethyl N-(1,3-dimyristoyloxypropan-2-yl)carbamate,
2-Dimethylaminoethyl N-(1,3-dipalmitoyloxypropan-2-yl)carbamate,
2-Dimethylaminoethyl N-(1,3-dioleoyloxypropan-2-yl)carbamate,
2-Dimethylaminoethyl N-(1,3-dilinolenyloxypropan-2-yl)carbamate,
2-Dimethylaminoethyl N-(1-oleoyloxy-3-palmitoyloxypropan-2-yl)carbamate,
2-Dimethylaminoethyl N-(1-linolenyloxy-3-oleoyloxypropan-2-yl)carbamate,
2-Diethylaminoethyl N-(1,3-dioleoyloxypropan-2-yl)carbamate,
3-Dimethylaminopropyl N-(1,3-dioleoyloxypropan-2-yl)carbamate,
2-Diisopropylaminoethyl N-(1,3-dioleoyloxypropan-2-yl)carbamate,
2-Di-n-propylaminoethyl N-(1,3-dioleoyloxypropan-2-yl)carbamate,
2-(N-Ethyl-N-methylamino)ethyl N-(1,3-dioleoyloxypropan-2-yl)carbamate,
2-Ethylaminoethyl N-(1,3-dioleoyloxypropan-2-yl)carbamate,
2-[N-Methyl-N-(2-hydroxyethyl)amino]ethyl N-(1,3-dioleoyloxypropan-2-yl)carbamate,
2-[N,N-Di-(2-hydroxyethyl)amino]ethyl N-(1,3-dioleoyloxypropan-2-yl)carbamate,
2-[N-(2-Diethylamino)ethyl-N-methylamino]ethyl N-(1,3-dioleoyloxypropan-2-yl)carbamate,
2-Piperidinoethyl N-(1,3-dioleoyloxypropan-2-yl)carbamate,
2-Pyrrolidinoethyl N-(1,3-dioleoyloxypropan-2-yl)carbamate
2-Aminoethyl N-(1,3-dioleoyloxypropan-2-yl)carbamate,
2-Dimethylaminoethyl N-(1,3-dioleoyloxypropan-2-yl)thiocarbamate,
2-Diethylaminoethyl N-(1,3-dioleoyloxypropan-2-yl)thiocarbamate,
2-[N,N-Di-(2-hydroxyethyl)amino]ethyl N-(1,3-dioleoyloxypropan-2-yl)thiocarbamate,
2-Pyrrolidinoethyl N-(1,3-dioleoyloxypropan-2-yl)thiocarbamate,
2-Dimethylaminoethyl N-(1,3-dioleoyloxypropan-2-yl)sulfamate,
2-Diethylaminoethyl N-(1,3-dioleoyloxypropan-2-yl)sulfamate,
2-[N,N-Di-(2-hydroxyethyl)amino]ethyl N-(1,3-dioleoyloxypropan-2-yl)sulfamate,
2-Pyrrolidinoethyl N-(1,3-dioleoyloxypropan-2-yl)sulfamate,
N-(2,3-Dioleoyloxy)propyl-4-dimethylaminobutylamide,
N-(2,3-Dioleoyloxy)propyl-4-diethylaminobutylamide,
N-(2,3-Dioleoyloxy)propyl-4-[N,N-di-(2-hydroxyethyl)amino]butylamide,
N-(2,3-Dioleoyloxy)propyl-4-pyrrolidinobutylamide.

Among compounds of general formula [I], 3-O-(4-dimethylaminobutanoyl)-1,2-O-dioleylglycerol, 3-O-(2-dimethylaminoethyl)carbamoyl-1,2-O-dioleylglycerol, 3-O-(2-diethylaminoethyl)carbamoyl-1,2-O-dioleylglycerol, 2-O-(2-diethylaminoethyl)carbamoyl-1,3-O-dioleoylglycerol, etc. are preferred. Particularly preferred is 3-O-(2-diethylaminoethyl)carbamoyl-1,2-O-dioleylglycerol.

The compound [I] can be obtained by the following and other processes.

(1) Where $R^1$ represents OY and A represents —O—C(=O)—NH—

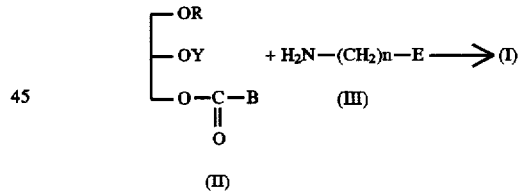

(wherein B is typically imidazolyl, halogen or phenoxy. The halogen may for example be chlorine, bromine or iodine. R, Y, E and n are as defined hereinbefore)

As shown schematically above, compound [I] can be synthesized by reacting [II] with [III].

This reaction between [II] and [III] can be carried out using 1–3 equivalents of [III] per equivalent of [II] in the presence of a solvent at 0° C.–150° C. for 1–20 hours. The reaction solvent that can be used includes dimethylformamide, pyridine, toluene, benzene, ether, dioxane, tetrahydrofuran, chloroform and so on. To hasten the reaction, a base such as triethylamine can be added. Moreover, [III] may be first converted to a metal salt using sodium hydride, n-butyllithium or the like in the above-mentioned solvent and, then, reacted with [II].

(2) Where $R^1$ represents OY and A represents —NH—C(=O)—O—

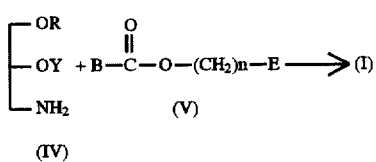

(wherein B, R, Y, E and n are as defined hereinbefore)

Compound [I] can be synthesized by reacting [IV] with [V] according to the above reaction schema, using reaction conditions similar to those mentioned under (1).

(3) Where $R^1$ represents OY and A represents —NH—C(=O)—O—

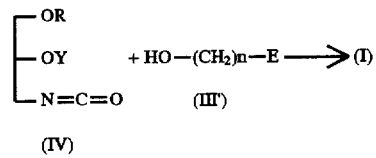

(wherein R, Y, E and n are as defined hereinbefore)

Compound [I] can be synthesized by reacting [VI] with [III'] as shown schematically above, using reaction conditions similar to those mentioned under (1).

(4) Where $R^1$ represents OY and A represents —O—C(=O)—NH—

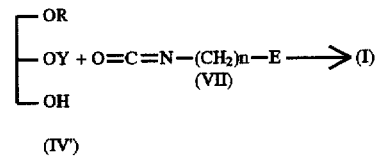

(wherein R, Y, E and n are as defined hereinbefore)

Compound [I] can be synthesized by reacting [IV'] with [VII] as shown schematically above, using reaction conditions similar to those mentioned under (1).

(5) Where $R^1$ represents OY and $R^2$ represents —A—$(CH_2)_n$-E

(wherein A, E and n are as defined hereinbefore)

Compound [I] can be synthesized by transforming the hydroxyl groups of the above compound into the substituent groups R and Y through reaction with suitable acylating agents (e.g. the anhydrides or acid chlorides of fatty acids). This route of synthesis is preferred where R and Y are fatty acid residues. <Synthesis of the starting compounds [IV], [IV'], [V], [VI], [VII], and [VIII]>

(1) Synthesis of Starting Compound [IV']

The starting compound [IV'] can be synthesized typically in accordance with the following reaction schema.

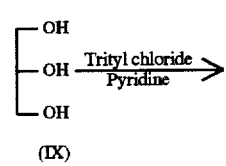

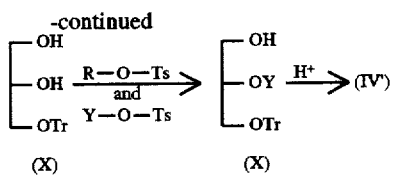

(wherein Tr represents trityl, Ts represents tosyl; R and Y are as defined hereinbefore)

(2) Synthesis of Starting Compound [IV]

The starting compound [IV] can be synthesized typically by the following exemplary process.

Starting with compound [IV'], the compound [IV] can be synthesized by the conventional procedure, e.g. azidation and subsequent reduction.

(3) Synthesis of Starting Compound [V]

The starting compound [V] wherein B is imidazolyl, for instance, can be synthesized by reacting compound [III'] with N,N'-carbonyldiimidazole in pyridine at ambient temperature.

(4) Synthesis of Starting Compound [VI]

The starting compound [VI] can be synthesized by reacting compound [IV] with diphosgene.

(5) Synthesis of Starting Compound [VII]

The starting compound [VII] can be easily synthesized typically by reacting compound [III] with diphosgene or by reacting a compound of the formula HOOC—$(CH_2)$n-E (where n and E are as defined hereinbefore) with DPPA (diphenylphosphoryl azide) in the presence of a tertiary amine such as triethylamine at 0°–150° C. and further in the presence of a tertiary amine such as pyridine at 0°–150° C.

(6) Synthesis of Starting Compound [VIII]

① The compound [VIII] wherein A represents —O—C(=O)—NH— can be synthesized typically according to the following reaction schema.

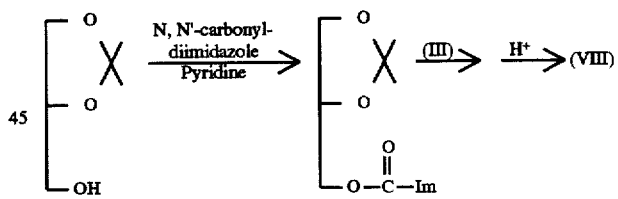

(wherein Im represents imidazolyl)

② The compound [VIII] wherein A represents —NH—C(=O)—O— can be synthesized typically according to the following reaction schema.

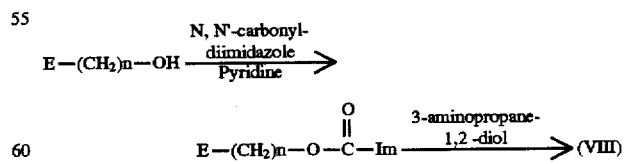

(wherein Im represents imidazolyl; E and n are as defined hereinbefore)

③ The compound [VIII] wherein A represents —O—C(=O)— can be synthesized typically according to the following reaction schema.

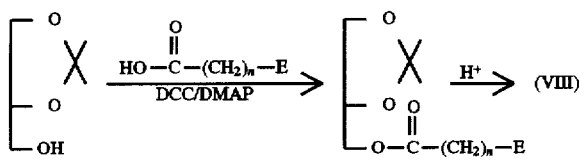

(wherein DCC means dicyclohexylcarbodiimide and DMAP means 4-N,N-dimethylaminopyridine; E and n are as defined hereinbefore)

④ The compound [VIII] wherein A represents —O—C(=S)—NH— can be synthesized typically according to the following reaction schema.

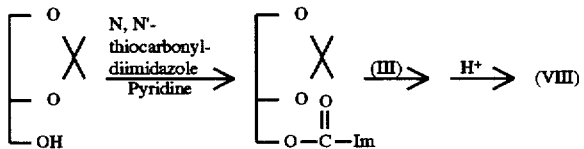

(wherein Im represents imidazolyl)

⑤ The compound [VIII] wherein A represents —NH—C(=O)— can be synthesized typically according to the following reaction schema.

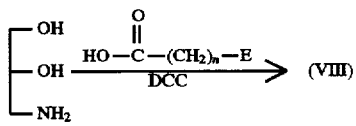

(wherein DCC means dicyclohexylcarbodiimide; E and n are as defined hereinbefore)

⑥ The compound [VIII] wherein A represents —OSO$_2$—NH— can be synthesized typically according to the following reaction schema.

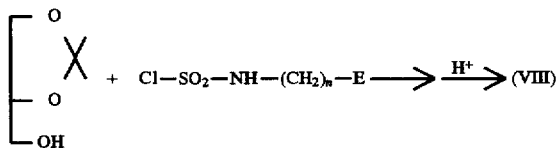

(wherein E and n are as defined hereinbefore)

⑦ The compound [VIII] wherein A represents —O—P(=O)(—CH$_3$)—O— can be synthesized typically according to the following reaction schema.

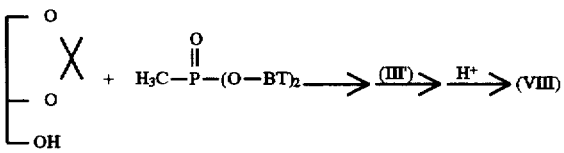

(wherein BT means 1-benzotriazolyl)

The phospholipid for use in combination with compound [I] may for example be phosphatidylethanolamine or phosphatidylcholine.

The constitutional ratio of compound [I] to phospholipid is appropriately 0.1:9.9–9.9:0.1 (compound [I]: phospholipid (molar ratio)), preferably 1:9–9:1 (compound [I]: phospholipid (molar ratio)), and for still better results, 1:3–3:1 (compound [I]: phospholipid (molar ratio)).

In the pharmaceutical composition according to the present invention (hereinafter referred to as composition of the invention), the lipid device may be any of lipid suspension, liposome and other forms.

The lipid device comprised of compound [I] and phospholipid can be simply prepared typically by admixing compound [I] with phospholipid in the presence of water. It can also be prepared by a process which comprises dissolving compound [I] and phospholipid in chloroform, removing the chloroform thoroughly under a blast of nitrogen gas, stirring the mixture well with addition of water, and subjecting it to sonication for several minutes.

The single-stranded nucleic acid copolymer may for example be poly(adenylic acid-uridylic acid), poly(inosinic acid-uridylic acid) or the like. The sequence of two constitutional bases may be regular or irregular. The term "regular" means that the two constituent bases are arranged alternately or a block formed by a given number of units of one base and that of the other base are alternate. Preferred is a single-stranded nucleic acid copolymer in which the two constituent bases are arranged alternately. Still more preferred is poly(adenylic acid-uridylic acid) of such alternate structure. The number of bases of the single-stranded nucleic acid copolymer that can be used in the practice of the present invention is not critically restricted but is suitably in the range of 10 to 5,000.

The single-stranded nucleic acid copolymer for use in accordance with the present invention may have undergone coalescence to form an apparent double-strand. Moreover, the single-stranded nucleic acid copolymer may have undergone partial coalescence to form a local double-strand.

The ratio of the lipid device to the single-stranded nucleic acid copolymer is preferably 1:0.1–1:10 (lipid device: single-stranded nucleic acid copolymer) by weight.

The composition of the invention can be manufactured by adding the single-stranded nucleic acid copolymer to the lipid device and stirring the mixture by suitable means. The composition may also be provided by adding the single-stranded nucleic acid copolymer in the course of preparation of the lipid device.

The composition of the invention is preferably administered in single dosage forms and can be applied to animals including man by the intravenous, intraarterial, oral, intratissue, local (e.g. transdermal) or rectal route. Particularly preferred are intravenous administration, intraarterial administration, and local administration. Of course, the composition is administered in dosage forms suitable for the respective routes, such as injections, peroral preparations, inhalants, eyedrops, ointments, suppositories and so on.

While the dosage of the composition of the invention is preferably determined in consideration of the species of active ingredient, dosage form, patient factors such as age and body weight, route of administration, nature and severity of disease, etc., the usual dosage for adults is generally 0.1 mg–10 g/day/man, preferably 1 mg–500 mg/day/man in terms of the active ingredient. A lower dosage may be sufficient in some cases, while a higher dosage may be needed in others. The dosage may be administered in a few divided doses or at intervals of a few days.

BEST MODE OF PRACTICING THE INVENTION

The following examples are intended to illustrate the present invention in further detail.

Reference Example 1

Synthesis of 1,2-O-dioleylglycerol (1) In 50 ml of pyridine was dissolved 4.6 g (50 mmol) of glycerol followed by addition of 13.9 g (50 mmol) of trityl chloride and the mixture was stirred at ambient temperature overnight. The reaction mixture was then concentrated under reduced pressure and the residue was diluted with water and extracted with ether. The organic layer was washed with water, dried over magnesium sulfate, and concentrated. The residue was purified by column chromatography (silica gel/chloroform-methanol) to provide 9.5 g (59%) of 1-O-tritylglycerol.

(2) In 120 ml of xylene was dissolved 3.22 g (10 mmol) of 1-O-tritylglycerol, followed by addition of 3.36 g (30 mmol) of t-butoxypotassium under argon. After 5 minutes of stirring, 30 ml of a solution of 12.8 g (30 mmol) oleyl p-toluenesulfonate in xylene was added dropwise and the mixture was stirred under reduced pressure (20–30 mmHg) at ambient temperature for 30 minutes and, then, at 50 for 1 hour. The reaction mixture was then poured in ice-water and extracted with ether, and the extract was washed with water, dried, and concentrated. The residue was purified by column chromatography (silica gel/n-hexane-ethyl acetate) to provide 6.10 g (73%) of 1,2-O-dioleyl-3-O-tritylglycerol.

(3) 1,2-O-Dioleyl-3-O-tritylglycerol (6.10 g, 7.3 mmol) was reacted with 5% trichloroacetic acid/methylene chloride (50 ml, w/v) at ambient temperature for 1 hour. The organic layer was then washed with saturated aqueous sodium hydrogen carbonate solution and water, dried, and concentrated. The residue was purified by column chromatography (silica gel/chloroform) to provide 3.75 g (87%) of the title compound.

$^1$H-NMR (200 MHz, CDCl$_3$) δ:0.88 (6H, t, J=6 Hz, C$\underline{H}_3$×2), 1.14–1.44 (44H, m, C$\underline{H}_2$×22), 1.48–1.68 (4H, m, OCH$_2$ C$\underline{H}_2$×2), 1.90–2.10 (8H, m, CH=CHC$\underline{H}_2$×4), 3.38–3.78 (9H, m, OC$\underline{H}_2$×4 & OCH), 5.26–5.45 (4H, m, C$\underline{H}$=C$\underline{H}$×2) MS (FAB): 593 (M+H)$^+$

Reference Example 2

Synthesis of 2,3-dioleyloxypropylamine (1) To a mixture of 1.00 g (1.7 mmol) of 1,2-O-dioleylglycerol, 0.83 g (17 mmol) of lithium azide, 0.89 g (3.4 mmol) of triphenylphosphine, and 1.13 g (3.4 mmol) of carbon tetrabromide was added 10 ml of N,N-dimethylformamide in bolus and the mixture was stirred at ambient temperature for 3 hours. After completion of the reaction, the solvent was distilled off and the residue was diluted with water and extracted with ether. The ether layer was washed with water, dried, and concentrated, and the residue was purified by column chromatography (silica gel/n-hexane-ethyl acetate) to provide 1.03 g (100%) of 2,3-dioleyloxypropyl azide as oil.

IR(neat, cm$^{-1}$): 2920, 2850, 2100

(2) In 30 ml of tetrahydrofuran was suspended 75 mg (2 mmol) of lithium aluminum hydride. While this suspension was held under ice-cooling, 1.03 g (1.7 mmol) of 2,3-dioleyloxypropyl azide was added dropwise and the mixture was stirred for 30 minutes. Then, the mixture was further stirred at ambient temperature for 2 hours. At completion of the reaction, the reaction mixture was poured in ice-water and extracted with ether and the extract was washed with water, dried, and concentrated. The residue was subjected to column chromatography (silica gel/methylene chloride-methanol) to provide 0.98 g (98%) of the title compound as colorless oil.

$^1$H-NMR (200 MHz, CDCl$_3$) δ:0.88 (6H, t, J=6 Hz, CH$_3$×2), 1.17–1.45 (44H, m, CH$_2$×22), 1.48–1.70 (4H, m, OCH$_2$ C$\underline{H}_2$×2), 1.90–2.14 (8H, m, CH=CHC$\underline{H}_2$×4), 2.64–2.91 (2H, m, NCH$_2$), 3.30–3.78 (9H, m, OC$\underline{H}_2$×3 & OCH), 5.25–5.46 (4H, m, CH=CH×2) MS (FAB): 592 (M+H)$^+$

Reference Example 3

Synthesis of 1,3-O-dioleylglycerol (1) In pyridine were dissolved 1.00 g (11 mmol) of glycerol and 2.96 g (43 mmol) of imidazole and azeotropic distillation was carried out. The residue obtained was dissolved in 15 ml of N,N-dimethylformamide. To this solution under ice-cooling was added 3.60 g (24 mmol) of tributyldimethylsilyl chloride, and the mixture was stirred at ambient temperature for 5 hours. After completion of the reaction, the solvent was distilled off and the residue was diluted with methylene chloride and washed with saturated aqueous sodium hydrogen carbonate solution. This was dried and concentrated to provide 3.45 g (99%) of 1,3-O-di-(t-butyldimethylsilyl)glycerol.

(2) In dioxane was dissolved 3.45 g (11 mmol) of 1,3-O-di-(t-butyldimethylsilyl)glycerol followed by addition of 3.03 g (12 mmol) of pyridinium p-toluenesulfonate. To this suspension was added 16.5 ml (22 mmol) of dihydrofuran gradually under ice-cooling and the mixture was stirred for 1 hour. After return to ambient temperature, the mixture was allowed to react overnight. After completion of the reaction, the solvent was distilled off and the residue was treated with methylene chloride and saturated aqueous sodium hydrogen carbonate solution. The methylene chloride layer was washed with water, dried, and concentrated to provide 4.25 g (100%) of 1,3-O-di-(t-butyldimethylsilyl)-2-O-tetrahydrofuranylglycerol.

(3) To a solution of 4.25 g (11 mmol) 1,3-O-di-(t-butyldimethylsilyl)-2-O-tetrahydrofuranylglycerol in 30 ml tetrahydrofuran was added 30 ml of tetra-n-butylammonium fluoride (1 mol/l in THF) dropwise and the mixture was stirred at ambient temperature for 2 hours. The reaction mixture was then concentrated and the residue was subjected to column chromatography (silica gel/methylene chloride-methanol) to provide 1.70 g (96%) of 2-O-tetrahydrofuranylglycerol.

(4) In 30 ml of xylene was dissolved 854 mg (5.3 mmol) of 2-O-tetrahydrofuranylglycerol. To this was added 1.78 g (15.9 mmol) of t-butoxypotassium under argon gas and the mixture was stirred for 5 minutes. Then, 10 ml of a solution of 6.71 g (15.9 mmol) oleyl p-toluenesulfonate in xylene was added dropwise and the mixture was stirred under reduced pressure (20–30 mmHg) at ambient temperature for 30 minutes and further at 50° C. for 1 hour. This reaction mixture was poured in ice-water and extracted with ether, and the extract was washed with water, dried, and concentrated. The residue was purified by column chromatography (silica gel/chloroform) to provide 628 mg (18%) of 1,3-O-dioleyl-2-O-tetrahydrofuranylglycerol as yellow oil.

(5) In 30 ml of tetrahydrofuran was dissolved 628 mg (0.95 mmol) of 1,3-O-dioleyl-2-O-tetrahydrofuranylglycerol followed by addition of 5 ml of diluted (10%) hydrochloric acid, and the mixture was stirred overnight. The reaction mixture was then diluted with water, neutralized with saturated aqueous sodium hydrogen carbonate solution, and extracted with ether. The extract was dried and concentrated and the residue was subjected to column chromatography (silica gel/n-hexane-ethyl acetate) to provide 321 mg (57%) of the title compound as colorless oil.

$^1$H-NMR (200 MHz, CDCl$_3$) δ:0.88 (6H, t, J=6 Hz, C$\underline{H}_3$×2), 1.14–1.26 (44H, m, C$\underline{H}_2$×22), 1.49–1.68 (4H, m, OCH$_2$ C$\underline{H}_2$×2), 1.98–2.13 (8H, m, CH=CHC$\underline{H}_2$×4), 3.37–3.56 (8H, m, OC$\underline{H}_2$×4), 3.95 (1H, brs, OC $\underline{H}$), 5.27–5.46 (4H, m, CH=CH×2) MS (FAB): 593 (M+H)$^+$

Reference Example 4

Synthesis of 1,3-dioleyloxy-2-propylamine (1) In 5 ml of pyridine was dissolved 150 mg (0.25 mmol) of 1,3-O-dioleylglycerol followed by addition of 77 mg (0.40 mmol) of p-toluenesulfonyl chloride and the mixture was heated at 60° C. and stirred for 2 days. After completion of the reaction, the solvent was distilled off and the residue was diluted with water and extracted with ether. The extract was dried and concentrated to provide 150 mg (80%) of 1,3-O-dioleyl-2-O-(p-toluenesulfonyl)glycerol as yellow oil.

(2) A mixture of 150 mg (80%) of the above 1,3-O-dioleyl-2-O-(p-toluenesulfonyl)glycerol, 30 mg (0.6 mmol) of lithium azide, and 5 ml of N,N-dimethylformamide was stirred at 100° C. for 2 hours. After cooling, the solvent was distilled off and the residue was diluted with water and extracted with ether. The extract was washed with water, dried, and concentrated to provide 125 mg (99%) of 1,3-dioleyloxy- 2-propyl azide as light-brown oil.

(3) In 3 ml of tetrahydrofuran was suspended 8 mg (0.2 mmol) of lithium aluminum hydride. While this suspension was maintained under ice-cooling, 125 mg (0.2 mmol) of 1,3-dioleyloxy-2-propyl azide was added dropwise and the mixture was stirred at 0° C. for 2 hours. The reaction mixture was then poured in ice-water and extracted with ether. The extract was washed with water, dried, and concentrated. The residue was subjected to column chromatography (silica gel/methylene chloride-methanol) to provide 104 mg (89%) of the title compound as colorless oil.

Reference Example 5

Synthesis of 1,2-O-dioleoylglycerol (1) In pyridine was dissolved 1 g (0.011 mol) of glycerin and azeotropic distillation was carried out. The residue was dissolved in 30 ml of pyridine, followed by addition of 4.05 g (0.012 mol) of dimethoxytrityl chloride under ice-cooling. The mixture was then stirred at ambient temperature overnight. After completion of the reaction, 5 ml of methanol was added and the mixture was stirred for 30 minutes, at the end of which time the solvent was distilled off. To the residue was added methylene chloride and the mixture was washed with saturated aqueous sodium hydrogen carbonate solution, dried, and concentrated. The residue was subjected to column chromatography (silica gel/methylene chloride-methanol, 0.1% pyridine) to provide 2.58 g (60.2%) of 1-O-dimethoxytritylglycerol.

(2) The 1-O-dimethoxytritylglycerol thus obtained, 290 mg (0.735 mmol was subjected to azeotropic distillation with pyridine and the residue was dissolved in 5 ml of pyridine. Then, 669 mg (2.223 mmol) of oleoyl chloride was added with ice-cooling and the reaction was carried out at 50° C. for 6 hours. After completion of the reaction, the solvent was distilled off under reduced pressure and the residue was diluted with methylene chloride, washed with saturated aqueous sodium hydrogen carbonate solution, dried, and concentrated. The residue was subjected to column chromatography (silica gel/n-hexane-methylene chloride) to provide 519 mg (76.5%) of 1-O-dimethoxytrityl-2,3-O-dioleoylglycerol.

$^1$H-NMR (60 MHz, CDCl$_3$) δ:0.88 (6H, m), 1.27 (40H, brs.), 1.50–1.70 (4H, m), 1.90–2.10 (8H, m), 3.10–3.30 (2H, m), 3.79 (6H, s), 4.20–4.40 (2H, m), 5.10–5.50 (5H, m), 6.70–7.40 (13H, m)

(3) The above 1-O-dimethoxytrityl-2,3-O-dioleoylglycerol, 218 mg (0.236 mmol), was dissolved in 10 ml of 5% formic acid-methylene chloride and the reaction was conducted for 10 minutes. The reaction mixture was then neutralized with saturated aqueous sodium hydrogen carbonate solution and the organic layer was further washed with saturated aqueous sodium hydrogen carbonate solution, dried, and concentrated. The residue was subjected to column chromatography (silica gel/n-hexane-methylene chloride-methanol) to provide 100 mg (68.0%) of the title compound.

$^1$H-NMR (200 MHz, CDCl$_3$) δ:0.88 (6H, t, J=6 Hz), 1.28 (40H, brs.), 1.50–1.70 (4H, m), 1.90–2.10 (8H, m), 2.28–2.40 (4H, m), 3.72 (2H, d, J=6 Hz), 4.10–4.40 (2H, m), 5.00–5.12 (1H, m), 5.30–5.40 (4H, m) MS (FAB): 621 (M+H)$^+$

Reference Example 6

Synthesis of 1,3-O-dioleoylglycerol (1) In 60 ml of pyridine was dissolved 2.75 g (0.013 mol) of 2-O-(t-butyldimethylsilyl)glycerol, followed by addition of 8.82 g (0.028 mol) of oleoyl chloride under ice-cooling. The reaction was conducted at 50° C. for 15 hours. After completion of the reaction, the solvent was distilled off and the residue was diluted with methylene chloride, washed with saturated aqueous sodium hydrogen carbonate solution, dried, and concentrated. The above procedure provided 1,3-O-dioleoyl-2-O-(t-butyldimethylsilyl)glycerol.

(2) To 1,3-O-dioleoyl-2-O-(t-butyldimethylsilyl)glycerol was added 266 ml of 0.1M tetra-n-butylammonium fluoride-tetrahydrofuran and the reaction was carried out at ambient temperature for 30 minutes. After completion of the reaction, the solvent was distilled off under reduced pressure and the residue was diluted with methylene chloride, washed with water, dried, and concentrated. The residue was subjected to column chromatography (silica gel/ethyl acetate-n-hexane) to provide 3.97 g (48.0% based on 2-O-t-butyldimethylsilylglycerol) of the title compound.

$^1$H-NMR (200 MHz, CDCl$_3$) δ:0.88 (6H, t, J=6 Hz), 1.28 (40H, brs.), 1.50–1.70 (4H, m), 1.90–2.10 (8H, m), 2.34 (4H, t, J=8 Hz), 4.10–4.22 (5H, m), 5.30–5.40 (4H, m) MS (FAB): 621 (M+H)$^+$

Reference Example 7

Synthesis of 1,3-O-dioleoyl-2-O-(2-bromoethyl) carbamoylglycerol (1) In pyridine was dissolved 230 mg (0.37 mmol) of 1,3-O-dioleoylglycerol and the solution was subjected to azeotropic distillation. The residue was dissolved in 5 ml of pyridine and after 120 mg (0.740 mmol) of N,N'-carbonyldiimidazole was added, the mixture was stirred at ambient temperature for 3 hours. The solvent was then distilled off under reduced pressure and the residue was dissolved in methylene chloride, washed with 5% sodium dihydrogen phosphate-water, dried, and concentrated. The residue was dissolved in 10 ml of N,N-dimethylformamide and after 45 mg (0.737 mmol) of 2-aminoethanol was added, the mixture was stirred at ambient temperature overnight. After completion of the reaction, the solvent was distilled off and the residue was dissolved in methylene chloride, washed with 5% sodium dihydrogen phosphate, dried, and concentrated. The residue was subjected to column chromatography (silica gel/methylene chloride-methanol) to provide 204 mg (79.5%) of 1,3-O-dioleoyl-2-O-(2-hydroxyethyl) carbamoylglycerol.

$^1$H-NMR (200 MHz, CDCl$_3$) δ:0.88 (6H, t, J=6 Hz), 1.28 (40H, brs.), 1.50–1.80 (4H, m), 1.90–2.10 (8H, m), 2.34

(4H, t, J=8 Hz), 3.28–3.40 (2H, m), 3.64–3.80 (2H, m), 4.20–4.40 (4H, m), 5.06–5.20 (2H, m), 5.30–5.50 (4H, m) MS (FAB): 690 (M—OH)$^+$ (2) To a mixture of 160 mg (0.226 mmol) 1,3-O-dioleoyl-2-O-(2-hydroxyethyl)carbamoylglycerol, 150 mg (0.452 mmol) of carbon tetrachloride, and 120 mg (0.458 mmol) of triphenylphosphine was added 10 ml of N,N-dimethylformamide in bolus and the mixture was stirred at ambient temperature for 2 hours. After completion of the reaction, the solvent was distilled off and the residue was dissolved in methylene chloride, washed with water, dried, and concentrated. The residue was subjected to column chromatography (silica gel/ethyl acetate-n-hexane) to provide 91 mg (52.2%) of the title compound.

$^1$H-NMR (200 MHz, CDCl$_3$) δ:0.86 (6H, t, J=6 Hz), 1.28 (4OH, brs.), 1.50–1.70 (4H, m), 1.90–2.10 (8H, m), 2.31 (4H, t, J=8 Hz), 3.40–3.52 (2H, m), 3.52–3.70 (2H, m), 4.20–4.44 (4H, m), 5.06–5.20 (2H, m), 5.25–5.40 (4H, m) MS (FAB): 770 (M+H)

Example of Synthesis-1

Synthesis of 3-O-(2-dimethylaminoethyl)carbamoyl-1,2-O-dioleylglycerol

To 25 ml of a solution of 2.00 g (3.4 mmol) of 1,2-O-dioleylglycerol in pyridine was added 0.66 g (4.1 mmol) of N,N'-carbonyldiimidazole and the mixture was stirred at ambient temperature for 5 hours. The solvent was then distilled off under reduced pressure and the residue was dissolved in methylene chloride, washed with 5% sodium dihydrogen phosphate-water, dried, and concentrated. The residue was dissolved in 20 ml of N,N-dimethylformamide, and after addition of 595 mg (6.8 mmol) of N,N-dimethylethylenediamine, the mixture was stirred overnight. After completion of the reaction, the solvent was distilled off and the residue was diluted with water and extracted with methylene chloride. The extract was washed with water, dried, and concentrated and the residue was subjected to column chromatography (silica gel/chloroform-methanol) to provide 2.18 g (91%) of the title compound.

$^1$H-NMR (200 MHz, CDCl$_3$) δ:0.88 (6H, t, J=7 Hz, CH$_3$×2), 1.16–1.44 (44H, m, CH$_2$×22), 1.47–1.68 (4H, m, OCH$_2$ C$\underline{H}_2$×2), 1.84–2.12 (8H, m, CH=CHC$\underline{H}_2$×4), 2.20 (6H, s, N(CH$_3$)$_2$), 2.39 (2H, t, J=6 Hz, NCH$_2$), 3.18–3.31 (2H, m, CONHC $\underline{H}_2$), 3.36–3.64 (7H, m, OC$\underline{H}_2$×3 & OCH), 4.03–4.26 (2H, m, CH$_2$OCO), 5.22 (1H, brs., NHCO), 5.28–5.43 (4H, m, CH=CH×2) MS (FAB): 707 (M+H)$^+$ Example of Synthesis-2

Synthesis of 3-O-(2-methylaminoethyl) carbamoyl-1,2-O-dioleylglycerol

The title compound was obtained in the same manner as Example of Synthesis-1 except that N-methylethylenediamine was used in lieu of N,N-dimethylethylenediamine.

$^1$H-NMR (200 MHz, CDCl$_3$) δ:0.88 (6H, t, J=6 Hz), 1.28 (44H, brs.), 1.50–1.60 (4H, m), 1.90–2.10 (8H, m), 2.43 (3H, s), 2.71 (2H, t, J=6 Hz), 3.28 (2H, q, J=6 Hz), 3.40–3.70 (7H, m), 4.05–4.26 (2H, m), 5.14 (1H, brs.), 5.30–5.44 (4H, m) MS (FAB): 693 (M+H)$^+$ Example of Synthesis-3

Synthesis of 3-O-(2-aminoethyl)carbamoyl-1,2-O-dioleylglycerol

The compound synthesized using N-tritylethylenediamine in lieu of N,N-dimethylethylenediamine in otherwise the same manner as Example of Synthesis-1 was treated with 5% trichloroacetic acid-methylene chloride and purified in the same manner to provide the title compound.

$^1$H-NMR (200 MHz, CDCl$_3$) δ:0.88 (6H, t, J=6 Hz), 1.28 (44H, brs.), 1.50–1.60 (4H, m), 1.90–2.10 (8H, m), 3.10–3.20 (2H, m), 3.40–3.70 (9H, m), 4.04–4.26 (2H, m), 5.30–5.45 (4H, m), 6.20 (1H, brs.) MS (FAB): 679 (M+H)$^+$ Example of Synthesis-4

Synthesis of 3-O-(2-diethylaminoethyl)carbamoyl-1,2-O-dioleylglycerol

Using N,N-diethylethylenediamine in lieu of N,N-dimethylethylenediamine, the procedure of Example of Synthesis-1 was otherwise repeated to provide the title compound.

$^1$H-NMR (200 MHz, CDCl$_3$m) δ:0.87 (6H, t, J=6 Hz), 1.01 (6H, t, J=6 Hz), 1.27 (44H, brs.), 1.46–1.62 (4H, m), 1.90–2.10 (8H, m), 2.48–2.62 (6H, m), 3.18–3.30 (2H, m), 3.38–3.66 (7H, m), 4.04–4.24 (2H, m), 5.24–5.44 (5H, m) MS (FAB): 735 (M+H)$^+$ Example of Synthesis-5

Synthesis of 3-O-(4-dimethylaminobutyl) carbamoyl-1,2-O-dioleylglycerol

Using 4-dimethylaminobutylamine in lieu of N,N-dimethylethylenediamine, the procedure of Example of Synthesis-1 was otherwise repeated to provide the title compound. $^1$H-NMR (200 MHz, CDCl$_3$) δ:0.88 (6H, t, J=6 Hz), 1.28 (44H, brs.), 1.46–1.70 (8H, m), 1.90–2.10 (8H, m), 2.39 (6H, s), 2.44–2.56 (2H, m), 3.10–3.24 (2H, m), 3.36–3.70 (7H, m), 4.00–4.24 (2H, m), 5.18–5.42 (5H, m) MS (FAB): 736 (M+H)$^+$ Example of Synthesis-6

Synthesis of 3-O-(2-dimethylaminoethyl) thiocarbamoyl-1,2-O-dioleylglycerol

Using N,N'-thiocarbonyldiimidazole in lieu of N,N'-carbonyldiimidazole, the procedure of Example of Synthesis-1 was otherwise repeated to provide the title compound.

$^1$H-NMR (200 MHz, CDCl$_3$) δ:0.88 (6H, t, J=6 Hz), 1.28 (44H, brs.), 1.50–1.60 (4H, m), 1.90–2.10 (8H, m), 2.21 (6H, d, J=4 Hz), 2.36–2.54 (2H, m), 3.30–3.80 (9H, m), 4.40–4.70 (2H, m), 5.26–5.45 (4H, m) MS (FAB): 723 (M+H)$^+$ Example of Synthesis-7

Synthesis of 3-O-(4-dimethylaminobutanoyl)-1,2-O-dioleylglycerol

In 6 ml of methylene chloride-N,N-dimethylformamide (1:2) was dissolved 120 mg (0.20 mmol) of 1,2-O-dioleylglycerol, followed by addition of 168 mg (1 mmol) of 4-dimethylaminobutyric acid hydrochloride. Then, 206 mg (1 mmol) of N,N'-dicyclohexylcarbodiimide (DCC) and 25 mg (0.2 mmol) of 4-dimethylaminopyridine were further added and the reaction was conducted at ambient temperature overnight. The precipitated byproduct urea was filtered off using a glass filter and the filtrate was concentrated to dryness under reduced pressure and treated with methylene chloride-saturated aqueous sodium hydrogen carbonate solution. After phase separation, the methylene chloride layer was dried over sodium sulfate and the solvent was distilled off under reduced pressure. The residue was subjected to column chromatography (silica gel/methylene chloride-methanol) to provide 123 mg (87%) of the title compound.

$^1$H-NMR (200 MHz, CDCl$_3$) δ:0.88 (6H, t, J=6 Hz), 1.20–1.40 (44H, m), 1.45–1.60 (4H, m), 1.70–1.90 (2H, m), 1.90–2.10 (8H, m), 2.22 (6H, s), 2.30 (2H, t, J=8 Hz), 2.36 (2H, t, J=8 Hz), 3.38–3.85 (7H, m), 4.04–4.30 (2H, m), 5.30–5.45 (4H, m) MS (FAB): 706 (M+H)$^+$

Example of Synthesis-8

Synthesis of 3-O-(N,N-dimethylaminoacetyl)-1,2-O-dioleylglycerol

In a solvent mixture of 22 ml N,N-dimethylformamide and 11 ml methylene chloride was suspended 572 mg (5.547 mmol) of N,N-dimethylglycine followed by addition of 1736 mg (8.414 mmol) of N,N'-dicyclohexylcarbodiimide and the mixture was stirred at ambient temperature overnight. The solvent was then distilled off under reduced pressure and the residue was dissolved in 12 ml of pyridine containing 327 mg (0.551 mmol) of dissolved 1,2-O-dioleylglycerol. Then, 80 mg (0.388 mmol) of N,N'-dicyclohexylcarbodiimide (DCC) was added and the reaction was conducted at 50° C. overnight. After completion of the reaction, the solvent was distilled off and the residue was dissolved in methylene chloride, washed with saturated aqueous sodium hydrogen carbonate solution, dried, and concentrated. The residue was subjected to column chromatography (silica gel/ethyl acetate-n-hexane) to provide 251 mg (67.2%) of the title compound.

$^1$H-NMR (200 MHz, CDCl$_3$) δ:0.88 (6H, t, J=6 Hz), 1.28 (44H, brs.), 1.50–1.70 (4H, m), 1.90–2.10 (8H, m), 2.36 (6H, s), 3.23 (2H, s), 3.40–3.70 (7H, m), 4.00–4.20 (2H, m), 5.20–5.40 (4H, m) MS (FAB): 678 (M+H)$^+$ Example of Synthesis-9

Synthesis of 3-O-(4-diethylaminobutanoyl)-1,2-O-dioleylglycerol (1) In 5 ml of anhydrous pyridine was dissolved 300 mg (0.51 mmol) of 1,2-O-dioleylglycerol, followed by addition of 188 mg (1.01 mmol) of 4-bromobutyl chloride under ice-cooling. After the temperature was allowed to return to ambient temperature, the reaction was conducted at 50° C. for 1 hour. The solvent was then distilled off and the residue was treated with methylene chloride-saturated aqueous sodium hydrogen carbonate solution. After phase separation and drying over sodium sulfate, the solvent was distilled off under reduced pressure. The residue thus obtained was subjected to column chromatography (silica gel/methylene chloride-methanol) to provide 159 mg (42%) of the bromo compound.

$^1$H-NMR (200 MHz, CDCl$_3$) δ:0.88 (6H, t, J=6 Hz), 1.27 (44H, brs.), 1.50–1.70 (4H, m), 1.90–2.20 (10H, m), 2.53 (2H, t, J=8 Hz), 3.40–3.70 (9H, m), 4.05–4.30 (2H, m), 5.25–5.45 (4H, m)

(2) In 6 ml of N,N-dimethylformamide-isopropyl alcohol-chloroform (1:1:1) was dissolved 130 mg (0.18 mmol) of the above bromo compound followed by addition of 1 ml of diethylamine and 70 mg (0.54 mmol) of N,N-diisopropylethylamine. The mixture was reacted at 60° C. for 20 hours and at 80° C. for a further 6 hours. The solvent was then distilled off under reduced pressure and the residue was treated with methylene chloride-water. The methylene chloride layer was dried over sodium sulfate and concentrated under reduced pressure. The residue was subjected to column chromatography (silica gel/methylene chloride-methanol) to provide 63 mg (50%) of the title compound.

$^1$H-NMR (200 MHz, CDCl$_3$) δ:0.88 (6H, t, J=6 Hz), 1.04 (6H, t, J=6 Hz), 1.27 (44H, brs.), 1.50–1.70 (4H, m), 1.80 (2H, m), 1.90–2.10 (8H, m), 2.37 (2H, t, J=6 Hz), 2.44–2.70 (6H, m), 3.40–3.70 (7H, m), 4.05–4.30 (2H, m), 5.30–5.45 (4H, m) MS (FAB): 734 (M+H)$^+$ Example of Synthesis-10

Synthesis of N-(2,3-dioleyloxy)propyl-4-dimethylaminobutylamide

In 3 ml of anhydrous N,N-dimethylformamide was dissolved 100 mg (0.17 mmol) of 2,3-dioleyloxypropylamine. To this solution were added 71 mg (0.42 mmol) of 4-dimethylaminobutyric acid hydrochloride, 105 mg (0.51 mmol) of N,N'-dicyclohexylcarbodiimide (DCC), and 4.1 mg (0.034 mmol) of 4-dimethylaminopyridine and the reaction was conducted at ambient temperature overnight. The reaction mixture was then treated as in Example of Synthesis-6 to provide 115 mg (96%) of the title compound.

$^1$H-NMR (200 MHz, CDCl$_3$) δ:0.88 (6H, t, J=6 Hz), 1.20–1.40 (44H, m), 1.50–1.60 (4H, m), 1.70–1.90 (2H, m), 1.90–2.10 (8H, m), 2.23 (6H, s), 2.24 (2H, t, J=8 Hz), 2.34 (2H, t, J=8 Hz), 3.20–3.60 (9H, m), 5.30–5.42 (4H, m) MS (FAB): 705 (M+H)$^+$

Example of Synthesis-11

Synthesis of 3-O-(2-dimethylaminoethyl)sulfamoyl-1,2-O-dioleylglycerol

In 4 ml of methylene chloride-pyridine (2:1) was dissolved 150 mg (0.25 mmol) of 1,2-O-dioleylglycerol. Then, 1 ml of a solution of 150 mg (0.75 mmol) (2-dimethylaminoethyl)sulfamoyl chloride in methylene chloride was added and the reaction was carried out at ambient temperature for 2 hours. After completion of the reaction, the solvent was distilled off under reduced pressure and the residue was treated with methylene chloride-saturated aqueous sodium hydrogen carbonate solution. The methylene chloride layer was dried over sodium sulfate and concentrated under reduced pressure. The residue was subjected to column chromatography (silica gel/methylene chloride-methanol) to provide 34 mg (18%) of the title compound. $^1$H-NMR (200 MHz, CDCl$_3$) δ:0.88 (6H, t, J=6 Hz), 1.20–1.40 (44H, m), 1.45–1.65 (4H, m), 1.90–2.10 (8H, m), 2.24 (6H, s), 2.48 (2H, t, J=6 Hz), 3.18 (2H, t, J=6 Hz), 3.40–3.60 (6H, m), 3.60–3.75 (1H, m), 4.08–4.30 (2H, m), 5.30–5.40 (4H, m) MS (FAB): 743 (M+H)$^+$ Example of Synthesis-12

Synthesis of 2-dimethylaminoethyl N-(2,3-dioleyloxypropyl)carbamate

In 2 ml of pyridine was dissolved 45 mg (0.5 mmol) of 2-dimethylaminoethanol followed by addition of 97 mg (0.6 mmol) of N,N'-carbonyldiimidazole and the mixture was stirred for 4 hours. To this solution was added 355 mg (0.6 mmol) of 2,3-dioleyloxypropylamine dropwise and the mixture was stirred for 24 hours. After completion of the reaction, the solvent was distilled off and the residue was dissolved in methylene chloride, washed with saturated aqueous sodium hydrogen carbonate, dried, and concentrated. The residue was purified by column chromatography (silica gel/methylene chloride-methanol) to provide 383 mg (100%) of the title compound.

$^1$H-NMR (200 MHz, CDCl$_3$) δ:0.87 (6H, t, J=6 Hz, CH$_3$×2), 1.12–1.44 (44H, m, CH$_2$×22), 1.46–1.64 (4H, m, OCH$_2$ CH$_3$×2), 1.88–2.12 (8H, m, CH=CHCH$_2$×4), 2.37 (6H, s, N(CH$_3$)$_2$), 2.54 (2H, t, J=6 Hz, NC H$_2$), 3.32–3.64 (9H, m, OCH$_2$×3, OCH and NHCH$_2$), 4.16 (2H, t, J=6 Hz, COOCH$_2$), 5.17 (1H, brs., NHCO), 5.26–5.46 (4H, m, CH=CH×2) MS (FAB): 707 (M+H)$^+$ Example of Synthesis-13

Synthesis of 2-O-(2-dimethylaminoethyl)carbamoyl-1,3-O-dioleylglycerol

To 2 ml of a solution of 150 mg (0.253 mmol) 1,3-O-dioleylglycerol in pyridine was added 82 mg (0.51 mmol) of N,N'-carbonyldiimidazole and the mixture was stirred at ambient temperature for 5 hours. The solvent was then distilled off under reduced pressure and the residue was dissolved in methylene chloride, washed with 5% sodium dihydrogen phosphate-water, dried, and concentrated. The residue was dissolved in 1.6 ml of N,N-dimethylformamide and stirred together with 45 mg (0.51 mmol) of N,N-dimethyl-ethylenediamine overnight. After completion of the reaction, the solvent was distilled off and the residue was diluted with water and extracted with methylene chloride. The extract was washed with water, dried, and concentrated. The residue was subjected to column chromatography (silica gel/chloroform-methanol) to provide 179 mg (100%) of the title compound.

$^1$H-NMR (200 MHz, CDCl$_3$) δ:0.88 (6H, t, J=6 Hz), 1.28 (44H, brs.), 1.50–1.65 (4H, m), 1.90–2.10 (8H, m), 2.20 (6H, s), 2.39 (2H, t, J=6 Hz), 3.20–3.30 (2H, m), 3.34–3.55 (4H, m), 3.55–3.70 (4H, d, J=4 Hz), 4.99 (1H, t, J=4 Hz), 5.25–5.46 (5H, m) MS (FAB): 707 (M+H)$^+$ Example of Synthesis-14

Synthesis of 2-dimethylaminoethyl N-(1,3-dioleyloxypropan-2-yl)carbamate

Using 1,3-dioleyloxy-2-propylamine, the procedure of Example of Synthesis-12 was otherwise repeated to provide the title compound.

$^1$H-NMR (200 MHz, CDCl$_3$) δ:0.88 (6H, t, J=6 Hz), 1.28 (44H, brs.), 1.50–1.60 (4H, m), 1.90–2.10 (8H, m), 2.28 (6H, s), 2.54 (2H, t, J=6 Hz), 3.40–3.55 (8H, m), 3.80–3.90 (1H, m), 4.15 (2H, t, J=6 Hz), 5.10–5.20 (1H, m), 5.20–5.45 (4H, m) MS (FAB): 707 (M+H)$^+$ Example of Synthesis-15

Synthesis of 3-O-(2-dimethylaminoethyl)carbamoyl-1,2-O-dioleoylglycerol

Using 1,2-O-dioleoylglycerol, the procedure of Example of Synthesis-1 was otherwise repeated to provide the title compound. $^1$H-NMR (200 MHz, CDCl$_3$) δ:0.88 (6H, t, J=6 Hz), 1.28 (40H, brs.), 1.50–1.70 (4H, m), 1.90–2.10 (8H, m), 2.22 (6H, s), 2.24–2.40 (4H, m), 2.41 (2H, t, J=6 Hz), 3.20–3.30 (2H, m), 4.10–4.15 (4H, m), 5.20–5.30 (2H, m), 5.30–5.45 (4H, m) MS (FAB): 735 (M+H)$^+$ Example of Synthesis-16

Synthesis of 2-O-(2-dimethylaminoethyl)carbamoyl-1,3-O-dioleoylglycerol

Using 1,3-O-dioleoylglycerol, the procedure of Example of Synthesis-13 was otherwise repeated to provide the title compound. $^1$H-NMR (200 MHz, CDCl$_3$) δ:0.88 (6H, t, J=6 Hz), 1.26 (40H, brs.), 1.50–1.70 (4H, m), 1.90–2.10 (8H, m), 2.22 (6H, s), 2.32 (4H, t, J=8 Hz), 2.42 (2H, t, J=6 Hz), 3.20–3.30 (2H, m), 4.12–4.25 (4H, m), 5.15 (1H, t, J=6 Hz), 5.20–5.45 (5H, m) MS (FAB): 735 (M+H)$^+$ Example of Synthesis-17

Synthesis of 2-dimethylaminoethyl N-( 2,3-dioleoyloxypropyl)carbamate

In 30 ml of anhydrous pyridine was dissolved 500 mg (5.61 mmol) of 2-dimethylaminoethanol followed by addition of 1.91 g (11.8 mmol) of N,N'-carbonyldiimidazole and the reaction was conducted at ambient temperature for 5 hours. To this reaction mixture was added 197 mg (2.16 mmol) of 3-amino-1,2-propanediol and the reaction was carried out at ambient temperature overnight. The pyridine was then distilled off under reduced pressure and the resulting crude carbamate was redissolved in anhydrous pyridine. Then, under ice-cooling, 5.22 g (17.4 mmol) of oleoyl chloride was added and the reaction was conducted at 50° C. for 14 hours. The pyridine was then distilled off under reduced pressure and the residue was dissolved in methylene chloride and washed with saturated aqueous sodium hydrogen carbonate solution. The methylene chloride layer was dried over sodium sulfate and concentrated. The residue was subjected to column chromatography (silica gel/methylene chloride-methanol) to provide 250 mg (16%) of the title compound.

$^1$H-NMR (200 MHz, CDCl$_3$) δ:0.88 (6H, t, J=6 Hz), 1.25 (40H, brs.), 1.50–1.70 (4H, m), 1.90–2.10 (8H, m), 2.28 (6H, s), 2.30 (4H, t, J=8 Hz), 2.57 (2H, t, J=6 Hz), 3.30–3.50 (2H, m), 4.06–4.30 (4H, m), 5.04–5.15 (2H, m), 5.25–5.40 (4H, m) MS (FAB): 735 (M+H)$^+$ Example of Synthesis-18

Synthesis of 2-dimethylaminoethyl N-(1,3-dioleoyloxypropan-2-yl)carbamate

Using 2-amino-1,3-propanediol in lieu of 3-amino-1,2-propanediol, the procedure of Example of Synthesis-17 was otherwise repeated to provide 372 mg (2.2 mmol) of the title compound. $^1$H-NMR (200 MHz, CDCl$_3$) δ:0.87 (6H, t, J=7 Hz), 1.20–1.40 (40H, m), 1.50–1.70 (4H, m), 1.90–2.10 (8H, m), 2.30 (6H, s), 2.32 (4H, t, J=8 Hz), 2.59 (2H, t, J=6 Hz), 4.00–4.25 (7H, m), 5.10–5.20 (1H, m), 5.30–5.45 (4H, m) MS (FAB): 735 (M+H)$^+$ Example of Synthesis-19

Synthesis of 2-O-(2-piperdinoethyl)carbamoyl-1,3-O-dioleoylglycerol

Using 1,3-O-dioleoylglycerol and 1-(2-aminoethyl)piperidine, the procedure of Example of Synthesis-13 was otherwise repeated to provide the title compound.

$^1$H-NMR (200 MHz, CDCl$_3$) δ:0.88 (6H, t, J=6 Hz), 1.28 (40H, brs.), 1.44–1.54 (2H, m), 1.54–1.76 (8H, m), 1.90–2.10 (8H, m), 2.32 (4H, t, J=8 Hz), 2.39–2.56 (6H, m), 3.20–3.40 (2H, m), 4.12–4.40 (4H, m), 5.08–5.24 (1H, m), 5.24–5.52 (5H, m) MS (FAB): 773 (M+H)$^+$ Example of Synthesis-20

Synthesis of 2-O-(2-diethylaminoethyl)carbamoyl-1,3-O-dioleoylglycerol

Using 1,3-O-dioleoylglycerol and N,N-diethylethylenediamine, the procedure of Example of Synthesis-13 was otherwise repeated to provide the title compound.

¹H-NMR (200 MHz, CDCl₃) δ:0.88 (6H, t, J=6 Hz), 1.02 (6H, t, 6 Hz), 1.28 (40H, brs.), 1.50–1.70 (4H, m), 1.90–2.10 (8H, m), 2.32 (4H, t, J=8 Hz), 2.44–2.66 (6H, m), 3.16–3.32 (2H, m), 4.22–4.38 (4H, m), 5.08–5.22 (1H, m), 5.26–5.52 (5H, m) MS (FAB): 763 (M+H)⁺

Example of Synthesis-21

Synthesis of 2-O-(2-diisopropylaminoethyl)carbamoyl-1,3-O-dioleoylglycerol

Using 1,3-O-dioleoylglycerol and N,N-diisopropylethylenediamine, the procedure of Example of Synthesis-13 was otherwise repeated to provide the title compound.

¹H-NMR (200 MHz, CDCl₃) δ:0.88 (6H, t, J=6 Hz), 1.00 (12H, t, 6 Hz), 1.27 (40H, brs.), 1.50–1.70 (4H, m), 1.90–2.10 (8H, m), 2.30 (4H, t, J=8 Hz), 2.48–2.64 (2H, m), 2.88–3.20 (4H, m), 4.10–4.32 (4H, m), 5.06–5.28 (2H, m), 5.30–5.42 (4H, m) MS (FAB): 791 (M+H)⁺

Example of Synthesis-22

Synthesis of 2-O-(2-pyrrolidinoethyl)carbamoyl-1,3-O-dioleoylglycerol

Using 1,3-O-dioleoylglycerol and 1-(2-aminoethyl)pyrrolidine, the procedure of Example of Synthesis-13 was otherwise repeated to provide the title compound.

¹H-NMR (200 MHz, CDCl₃) δ:0.88 (6H, t, J=6 Hz), 1.27 (40H, brs.), 1.50–1.70 (4H, m), 1.74–1.88 (4H, m), 1.90–2.10 (8H, m), 2.30 (4H, t, J=8 Hz), 2.44–2.70 (6H, m), 3.20–3.40 (2H, m), 4.20–4.42 (4H, m), 5.08–5.22 (1H, m), 5.24–5.46 (5H, m) MS (FAB): 761 (M+H)⁺

Example of Synthesis-23

Synthesis of 2-O-(2-morpholinoethyl)carbamoyl-1,3-O-dioleoylglycerol

Using 1,3-O-dioleoylglycerol and 4-(2-aminoethyl)morpholine, the procedure of Example of Synthesis-13 was otherwise repeated to provide the title compound.

¹H-NMR (200 MHz, CDCl₃) δ:0.88 (6H, t, J=6 Hz), 1.27 (40H, brs.), 1.50–1.70 (4H, m), 1.90–2.10 (8H, m), 2.31 (4H, t, J=8 Hz), 2.40–2.54 (6H, m), 3.20–3.40 (2H, m), 3.70 (4H, t, J=6 Hz), 4.12–4.38 (4H, m), 5.08–5.20 (2H, m), 5.20–5.46 (4H, m) MS (FAB): 777 (M+H)⁺

Example of Synthesis-24

Synthesis of 2-O-(3-diethylaminopropyl)carbamoyl-1,3-O-dioleoylglycerol

Using 1,3-O-dioleoylglycerol and 3-diethylaminopropylamine, the procedure of Example of Synthesis-13 was otherwise repeated to provide the title compound.

¹H-NMR (200 MHz, CDCl₃) δ:0.88 (6H, t, J=6 Hz), 1.03 (6H, t, 6 Hz), 1.28 (40H, brs.), 1.50–1.70 (4H, m), 1.90–2.10 (8H, m), 2.30 (4H, t, J=8 Hz), 2.46–2.58 (6H, m), 3.20–3.32 (2H, m), 4.10–4.34 (4H, m), 5.10–5.20 (1H, m), 5.30–5.42 (4H, m), 6.18–6.30 (1H, brs.) MS (FAB): 777 (M+H)⁺

Example of Synthesis-25

Synthesis of 2-O-[2-(N-methyl-N-(2-hydroxyethyl)amino)ethyl]carbamoyl-1,3-O-dioleoylglycerol In 10 ml of chloroform was dissolved 173 mg (0.224 mmol) of 1,3-O-dioleoyl-2-O-(2-bromoethyl)carbamoylglycerol followed by addition of 543 mg (7.228 mmol) of 2-(methylamino)ethanol and 27 mg (0.209 mmol) of diisopropylethylamine and the mixture was refluxed at 80° C. overnight. The reaction mixture was then washed with 5% sodium dihydrogen phosphate-H₂O, dried, and concentrated. The residue was subjected to column chromatography (silica gel/methylene chloride-methanol) to provide 128 mg (74.3%) of the title compound.

¹H-NMR (200 MHz, CDCl₃) δ:0.86 (6H, t, J=6 Hz), 1.27 (40H, brs.), 1.50–1.70 (4H, m), 1.90–2.10 (8H, m), 2.26–2.38 (7H, m), 2.50–2.70 (4H, m), 3.20–3.40 (2H, m), 3.61 (4H, t, J=6 Hz), 4.20–4.44 (4H, m), 5.06–5.20 (2H, m), 5.30–5.45 (4H, m) MS (FAB): 765 (M+H)⁺

Example of Synthesis-26

Synthesis of 2-O-[2-(N-ethyl-N-(2-hydroxyethyl)amino)ethyl]carbamoyl-1,3-O-dioleoylglycerol Using 2-(ethylamino)ethanol, the procedure of Example of Synthesis-25 was otherwise repeated to provide the title compound.

¹H-NMR (200 MHz, CDCl₃) δ:0.88 (6H, t, J=6 Hz), 1.03 (3H, t, 6 Hz), 1.28 (40H, brs.), 1.50–1.70 (4H, m), 1.90–2.10 (8H, m), 2.32 (4H, t, J=8 Hz), 2.54–2.68 (6H, m), 3.20–3.30 (2H, m), 3.56 (2H, t, J=6 Hz), 4.12–4.34 (4H, m), 5.06–5.20 (2H, m), 5.30–5.44 (4H, m) MS (FAB): 779 (M+H)⁺

Example of Synthesis-27

Synthesis of 2-O-[2-(N,N-di-(2-hydroxyethyl)amino)ethyl]carbamoyl-1,3-O-dioleoylglycerol Using diethanolamine, the procedure of Example of Synthesis-25 was otherwise repeated to provide the title compound.

¹H-NMR (200 MHz, CDCl₃) δ:0.88 (6H, t, J=6 Hz), 1.28 (40H, brs.), 1.50–1.70 (4H, m), 1.90–2.10 (8H, m), 2.32 (4H, t, J=8 Hz), 2.60–2.70 (6H, m), 3.20–3.30 (2H, m), 3.60 (4H, t, J=6 Hz), 4.12–4.40 (4H, m), 5.08–5.20 (1H, m), 5.30–5.42 (4H, m), 5.60–5.70 (1H, brs.) MS (FAB): 795 (M+H)⁺

Example of Synthesis-28

Synthesis of 2-O-[2-(N-methyl-N-n-butylamino)ethyl]carbamoyl-1,3-O-dioleoylglycerol Using N-methylbutylamine, the procedure of Example of Synthesis-25 was otherwise repeated to provide the title compound. ¹H-NMR (200 MHz, CDCl₃) δ:0.82–0.96 (9H, m), 1.10–1.50 (42H, m), 1.50–1.75 (6H, m), 1.90–2.10 (8H, m), 2.19 (3H, s), 2.26–2.40 (6H, m), 2.46 (2H, m), 3.20–3.30 (2H, m), 4.10–4.30 (4H, m), 5.08–5.20 (1H, m), 5.25–5.40 (4H, m) MS (FAB): 777 (M+H)⁺

Example of Synthesis-29

Synthesis of 2-O-[2-(4-(2-hydroxyethyl)piperazino)ethyl]carbamoyl-1,3-O-dioleoylglycerol Using 1-(2-hydroxyethyl)piperazine, the procedure of Example of Synthesis-25 was otherwise repeated to provide the title compound.

¹H-NMR (200 MHz, CDCl₃) δ:0.88 (3H, t, J=6 Hz), 1.28 (40H, brs.), 1.50–1.70 (4H, m), 1.90–2.10 (8H, m), 2.32 (4H, t, J=8 Hz), 2.40–2.60 (12H, m), 3.18–3.32 (2H, m), 3.62 (2H, t, J=6 Hz), 4.12–4.32 (4H, m), 5.08–5.24 (2H, m), 5.30–5.40 (4H, m) MS (FAB): 820 (M+H)⁺

Example of Synthesis-30

Synthesis of 2-O-[2-(N,N,N',N'-tetramethylguanidino)ethyl]carbamoyl-1,3-O-dioleoylglycerol Using N,N,N',N'-teramethylguanidine, the procedure of Example of Synthesis-25 was otherwise repeated to provide the title compound.

$^1$H-NMR (200 MHz, CDCl$_3$) δ:0.88 (3H, t, J=6 Hz), 1.27 (40H, brs.), 1.50–1.70 (4H, m), 1.90–2.10 (8H, m), 2.30 (4H, t, J=8 Hz), 2.96 (3H, s), 3.10 (3H, s), 3.35–3.40 (2H, m), 3.60–3.70 (2H, m), 4.04–4.34 (4H, m), 4.98–5.08 (1H, m), 5.30–5.40 (4H, m), 6.30–6.40 (1H, m) MS (FAB): 805 (M+H)$^+$

Example of Synthesis-31

Synthesis of 2-O-[2-(N-( 2-diethylamino)ethyl-N-methylamino)ethyl]carbamoyl-1,3-O-dioleoylglycerol Using N,N-diethyl-N'-methylethylenediamine, the procedure of Example of Synthesis-25 was otherwise repeated to provide the title compound. $^1$H-NMR (200 MHz, CDCl$_3$) δ:0.88 (6H, t, J=6 Hz), 1.04 (6H, t, J=6 Hz), 1.26 (40H, brs.), 1.50–1.70 (4H, m), 1.90–2.10 (8H, m), 2.26–2.36 (7H, m), 2.44–2.64 (10H, m), 3.15–3.25 (2H, m), 4.16–4.26 (4H, m), 5.08–5.18 (1H, m), 5.30–5.40 (4H, m), 6.46–6.60 (1H, brs.) MS (FAB): 820 (M+H)$^+$

Example of Synthesis-32

Synthesis of 2-O-[2-(4-ethylpiperazino)ethyl] carbamoyl-1,3-O-dioleoylglycerol

Using 1-ethylpiperazine, the procedure of Example of Synthesis-25 was otherwise repeated to provide the title compound.

$^1$H-NMR (200 MHz, CDCl$_3$) δ:0.88 (6H, t, J=6 Hz), 1.10 (3H, t, J=6 Hz), 1.26 (40H, brs.), 1.50–1.70 (4H, m), 1.90–2.10 (8H, m), 2.32 (4H, t, J=8 Hz), 2.38–2.60 (12H, m), 3.22–3.34 (2H, m), 4.12–4.34 (4H, m), 5.10–5.30 (2H, m), 5.30–5.42 (4H, m) MS (FAB): 802 (M+H)$^+$

Example of Synthesis-33

Synthesis of 2-O-[2-(N-ethyl-N-methylamino)ethyl] carbamoyl-1,3-O-dioleoylglycerol In 3 ml of chloroform was dissolved 131 mg (0.170 mmol) of 1,3-O-dioleoyl-2-O-(2-bromoethyl) carbamoylglycerol followed by addition of 470 mg (7.951 mmol) of N-ethylmethylamine and the reaction was conducted in a sealed tube at 80° C. overnight. This reaction mixture was then washed with 5% sodium dihydrogen phosphate-H$_2$O, dried and concentrated. The residue was subjected to column chromatography (silica gel/methylene chloride-methanol) to provide 104 mg (81.5%) of the title compound.

$^1$H-NMR (200 MHz, CDCl$_3$) δ:0.88 (6H, t, J=6 Hz), 1.04 (3H, t, J=6 Hz), 1.26 (40H, brs.), 1.50–1.70 (4H, m), 1.90–2.10 (8H, m), 2.20 (3H, s), 2.32 (4H, t, J=8 Hz), 2.38–2.52 (4H, m), 3.20–3.30 (2H, m), 4.12–4.32 (4H, m), 5.10–5.20 (1H, m), 5.25–5.42 (5H, m) MS (FAB): 749 (M+H)$^+$

Example of Synthesis-34

Synthesis of 2-O-(2-diethylaminoethyl)carbamoyl-1,3-O-dipalmitoylglycerol

Using 1,3-O-dipalmitoylglycerol and N,N-diethylethylenediamine, the procedure of Example of Synthesis-13 was otherwise repeated to provide the title compound.

$^1$H-NMR (200 MHz, CDCl$_3$) δ:0.87 (6H, t, J=6 Hz), 1.00 (6H, t, J=6 Hz), 1.25 (48H, brs.), 1.50–1.70 (4H, m), 2.30 (4H, t, J=8 Hz), 2.46–2.60 (6H, m), 3.10–3.30 (2H, m), 4.12–4.32 (4H, m), 5.10–5.20 (1H, m), 5.20–5.35 (1H, m) MS (FAB): 711 (M+H)$^+$

Example of Synthesis-35

Synthesis of 2-diethylaminoethyl N-(1,3-dioleoyloxypropan-2-yl)carbamate

In methylene chloride was dissolved 470 mg (4 mmol) of 2-diethylaminoethanol. After addition of 633 mg (8 mmol) of pyridine, 690 mg (4.4 mmol) of phenyl chloroformate was further added under ice-cooling and the reaction was conducted at ambient temperature for 2 hours. After completion of the reaction, the solvent was distilled off and the residue was transferred into ethyl acetate-1% aqueous sodium hydrogen carbonate solution. The ethyl acetate layer was separated, dried over sodium sulfate, and concentrated under reduced pressure to give 705 mg (74%) of crude carbonate compound. This crude carbonate was dissolved in anhydrous pyridine followed by addition of 134 mg (1.47 mmol) of 2-amino-1,3-propanediol and the reaction was carried out at 80° C. overnight. Then, 973 mg (3.2 mmol) of oleoyl chloride was added and the reaction was further conducted at ambient temperature for 24 hours. After completion of the reaction, the solvent was distilled off under reduced pressure and the residue was transferred into methylene chloride-saturated aqueous sodium hydrogen carbonate solution and dried over sodium sulfate. The solvent was then removed under reduced pressure and the residue was subjected to column chromatography (silica gel/methylene chloride-methanol) to provide 250 mg (22%) of the title compound.

$^1$H-NMR (200 MHz, CDCl$_3$) δ:0.87 (6H, t, J=6 Hz), 1.04 (6H, t, J=6 Hz), 1.28 (40H, brs.), 1.50–1.70 (4H, m), 1.90–2.10 (8H, m), 2.30 (4H, t, J=8 Hz), 2.50–2.70 (6H, m), 4.00–4.30 (7H, m), 5.05–5.20 (1H, m), 5.25–5.45 (4H, m) MS (FAB): 763 (M+H)$^+$

Example of Synthesis-36

Synthesis of 2-O-(3-diethylaminopropionyl)-1,3-O-dioleoylglycerol

In a solvent mixture of 3 ml N,N-dimethylformamide and 6 ml methylene chloride was dissolved 172 mg (0.277 mmol) of 1,3-dioleoylglycerol followed by addition of 101 mg (0.556 mmol) of N,N-diethyl-β-alanine (hydrochloride), 114 mg (0.553 mmol) of N,N-dicyclohexylcarbodiimide, and 7 mg (0.057 mmol) of 4-dimethylaminopyridine and the mixture was stirred overnight. This reaction mixture was then filtered and the filtrate was concentrated under reduced pressure. The residue was dissolved in methylene chloride and washed with water. The washed solution was dried and concentrated and the residue was subjected to column chromatography (silica gel/methylene chloride-methanol) to provide 129 mg (62%) of the title compound.

$^1$H-NMR (200 MHz, CDCl$_3$) δ:0.88 (6H, t, J=6 Hz), 1.20–1.40 (46H, m), 1.50–1.70 (4H, m), 1.90–2.10 (8H, m), 2.32 (4H, t, J=8 Hz), 2.76–2.84 (6H, m), 3.04–3.14 (2H, m), 4.08–4.42 (4H, m), 5.18–5.30 (1H, m), 5.30–5.44 (4H, m) MS (FAB): 748 (M+H)$^+$

Example of Synthesis-37

Synthesis of O-(2-dimethylaminoethyl),O'-(1,3-dioleoyloxypropyl)methylphosphonate To 310 mg (0.50 mmol) of 1,3-dioleoylglycerol dried by azeotropic distillation with pyridine was added 9.1 ml (1 mmol) of 0.11M methyl bis-O,O-(1-benzotriazolyl) phosphonate-dioxane and the reaction was conducted at ambient temperature for 3 hours. To this reaction mixture were added 446 mg (5 mmol) of 2-dimethylaminoethanol and 411 mg (5 mmol) of 1-methylimidazole and the reaction was further conducted at ambient temperature overnight. The reaction mixture was then treated with methylene chloride-5% sodium dihydrogen phosphate solution and the methylene chloride layer was dried over sodium sulfate and concentrated under educed pressure. The residue was subjected to column chromatography (silica gel/methylene chloride-methanol) to provide 272 mg (59%) of the title compound.

$^1$H-NMR (200 MHz, CDCl$_3$) δ:0.86 (6H, t, J=6 Hz), 1.25 (40H, brs), 1.54 (3H, d, J=20 Hz), 1.50–1.70 (4H, m), 2.32 (4H, t, J=8 Hz), 2.35 (6H, s), 2.68 (2H, t, J=6 Hz), 4.05–4.25 (4H, m), 4.25–4.35 (2H, m), 4.70–4.90 (1H, m), 5.25–5.40 (4H, m) MS (FAB): 770 (M+H)$^+$ Example of Synthesis-38

Synthesis of O-(2-aminoethyl)-O'-(1,3-dioleoyloxypropyl)methylphosphonate

Using t-butyl N-(2-hydroxyethyl)carbamate in lieu of 2-dimethylaminoethanol, the procedure of Example of Synthesis-37 was otherwise repeated and the resulting compound was treated with trifluoroacetic acid/methylene chloride (1:2) to provide the title compound.

$^1$H-NMR (200 MHz, CDCl$_3$) δ:0.88 (6H, t, J=6 Hz), 2.25 (40H, brs), 1.50–1.90 (7H, m), 1.90–2.10 (8H, m), 2.34 (4H, t, J=8 Hz), 3.30–3.40 (2H, s), 4.10–4.50 (6H, m), 4.75–4.90 (1H, m), 5.30–5.40 (4H, m) MS (FAB): 742 (M+H)$^+$ Example of Synthesis-39

Synthesis of O-(2-diethylaminoethyl)-O'-(1,3-dioleoyloxypropyl)methylphosphonate Using 2-diethylaminoethanol, the procedure of Example of Synthesis-37 was otherwise repeated to provide 166 mg (70.7%) of the title compound.

$^1$H-NMR (200 MHz, CDCl$_3$) δ:0.87 (6H, t, J=6 Hz), 1.01 (6H, t, J=6 Hz), 1.26 (40H, brs), 1.48–1.70 (7H, m), 1.90–2.10 (8H, m), 2.32 (4H, t, J=8 Hz), 2.57 (4H, q, J=6 Hz), 2.80 (2H, t, J=6 Hz), 3.90–4.40 (6H, m), 4.70–4.90 (1H, m), 5.30–5.42 (4H, m) MS (FAB): 798 (M+H)$^+$ Production Example 1

In 200 μl of chloroform, in a vial, were dissolved 5 mg of the compound according to Example of Synthesis-4 and 5 mg of egg yolk phosphatidylethanolamine. Then, nitrogen gas was blasted against the solution.to remove the chloroform, leaving a thin film on the internal wall of the vial. The vial was then allowed to stand overnight under reduced pressure and after addition of 2 ml of sterile distilled water, was agitated in a vortex mixer to exfoliate the thin film. After purging with nitrogen gas, the vial was hermetically stoppered and allowed to stand at 4° C. for 3 hours. Then, sonication was carried out for 10 minutes with a bath sonicator to provide a lipid device.

Production Example 2

Using the compound according to Example of Synthesis-1, a lipid device was prepared in otherwise the same manner as Production Example 1.

Production Example 3

Using the compound according to Example of Synthesis-7, a lipid device was prepared in otherwise the same manner as Production Example 1.

Production Example 4

In 200 l of chloroform, in a vial, were dissolved 5 mg of the compound according to Example of Synthesis-20 and 5 mg of egg yolk phosphatidylcholine. Then, nitrogen gas was blasted against the solution to remove the chloroform, leaving a thin film on the internal wall of the vial. The vial was then allowed to stand overnight under reduced pressure and after addition of 2 ml of sterile distilled water, was agitated in a vortex mixer to exfoliate the thin film. After purging with nitrogen gas, the vial was hermetically stoppered and allowed to stand at 4° C. for 3 hours. Then, sonication was carried out for 10 minutes with a bath sonicator to provide a lipid device.

Production Example 5

Using the compound according to Example of Synthesis-1, a lipid device was prepared in otherwise the same manner as Production Example 4.

Production Example 6

Using the compound according to Example of Synthesis-4, a lipid device was prepared in otherwise the same manner as Production Example 4.

Production Example 7

Using the compound according to Example of Synthesis-7, a lipid device was prepared in otherwise the same manner as Production Example 4.

Example 1

An alternate poly(adenylic acid-uridylic acid)-containing injectable composition To 60 μl of the lipid device according to Production Example 4 was added 0.9 ml of physiological saline solution, followed by addition of 0.1 ml of a 100 μg/ml saline solution of an alternate poly(adenylic acid-uridylic acid) [Poly(rA-rU)• Poly(rA-rU), S20, w=4.70, manufactured by Pharmacia; the same applies hereinafter], and the mixture was stirred to provide an injectable composition. Similar injectable compositions were prepared using the lipid devices according to Production Examples 1–3 and 5–7.

Example 2

An alternate poly(adenylic acid-uridylic acid)-containing injectable composition To 300 μl of Lipofectin (trademark, Bethesda Laboratories) was added 0.9 ml of physiological saline, followed by addition of 0.1 ml of a 100 μg/ml saline solution of the alternate polymer and the mixture was stirred to provide an injectable composition.

Test Example 1

HeLaS3 cell growth inhibitory action (in vitro)

A 96-well plate was seeded with HeLaS3 cells at a cell density of 10$^4$ cells/well (90 μl). On the following day, 10 μl of the 30 μg/ml lipid device containing a varying concentration of alternate poly(adenylic acid-uridylic acid) was added to each well. As to the composition containing Genetransfer (trademark, Wako Pure Chemical Industries), 1 ml of 10 mM phosphate buffer (supplemented with 0.9% sodium chloride) containing 20 μg of dissolved alternate poly (adenylic acid-uridylic acid) was added into each vial of Genetransfer and this was used as diluted to predetermined concentrations of alternate poly(adenylic acid-uridylic acid). The plate was incubated for 72 hours after addition and, then, 10 μl per well of a 5 mg/ml solution of MTT (3-(4,5-dimethylthiazol-2-yl)-2,5-diphenyltetrazolium bromide was added. After 2–4 hours, the reaction was stopped by adding isopropyl alcohol/0.04N hydrochloric acid mixture. After each well was agitated, the absorbance at 540 nm was measured with a plate reader (manufactured by Corona) and the percentage HeLaS3 cell growth inhibition (%) was calculated. This calculation was performed according to the equation given below. The cell growth inhibition rate of the single-stranded nucleic acid copolymer in the absence of the lipid device was taken as control.

$$\% \text{ Inhibition} = \left(1 - \frac{\text{Cell count in presence of sample}}{\text{Cell count in presence of saline}}\right) \times 100$$

The results are shown in Table 1.

TABLE 1

| Concn. of poly(A-U) (ng/ml) | % Inhibition | | |
|---|---|---|---|
| | Control | genetransfer | Exp. of Syn.-1 + EPE |
| 0 | 0 | 0 | 0 |
| 0.1 | 0 | 15 | 1 |
| 1 | 0 | 0 | 36 |
| 10 | 0 | 32 | 91 |
| 100 | 0 | 82 | 100 |

| Concn. of poly(A-U) (ng/ml) | % Inhibition | | | |
|---|---|---|---|---|
| | Exp. of Syn.-4 | | Exp. of Syn.-20 | |
| | +EPE | +ELC | +EPE | +ELC |
| 0 | 0 | 0 | 0 | 0 |
| 0.1 | 0 | 0 | 25 | 25 |
| 1 | 0 | 0 | 62 | 62 |
| 10 | 61 | 65 | 89 | 89 |
| 100 | 100 | 91 | 100 | 100 | genetransfer: trademark, Wako Pure Chemical Industries
EPE; egg yolk phosphatidylethanolamine
ELC; egg yolk phosphatidylcholine
Exp. of Syn. = Example of Synthesis It is apparent from Table 1 that when applied together with the lipid device, the single-stranded nucleic acid copolymer [alternate poly(adenylic acid-uridylic acid)] which is not effective when used alone shows cell growth inhibitory activity.

Test Example 2

Induction of β-interferon from HeLaS3 cells

A 96-well plate was seeded with $10^4$ cells/well of HeLaS3 cells (90 μl) and on the following day 10 μl of the 30 μg/ml lipid device containing a varying concentration of alternate poly(adenylic acid-uridylic acid) was added to each well. The plate was incubated for 24 hours after addition and the β-interferon in the cell culture was determined using an ELISA kit (for assay of β-interferon, manufactured by Toray Industries, Inc.). The results are shown in Table 2.

TABLE 2

| Concn. of poly (A-U) (ng/ml) | IU/ml | |
|---|---|---|
| | Control | Exp. of Syn.-4 + EPE |
| 0 | 0 | 0 |
| 0.1 | 0 | 10 |
| 1 | 0 | 34 |
| 10 | 0 | 32 |
| 100 | 0 | 148 |

EPE; egg yolk phosphatidylethanolamine
Exp. of Syn.-4 = Example of Synthesis-4

What is claimed is:

1. A composition comDrisinq a lipid device and a single-stranded nucleic acid copolymer, wherein said lipid device is a mixture of a phospholipid and a compound of the following general formula

wherein $R^1$ and $R^2$ are not the same and each represents OY or —A—$(CH_2)$n-E. n represents a whole number of 0–4. E represents pyrrolidino, piperidino, substituted or unsubstituted piperazino, morpholino, substituted or unsubstituted guanidino, or

($R^3$ and $R^4$ are the same or different and each represents hydrogen, lower($C_{1-4}$) alkyl, hydroxy-lower($C_{1-4}$) alkyl, or mono- or di-(lower) alkylaminoalkyl($C_{2-6}$)). A represents the following 1, 2, 3, 4, 5, 6, or 7

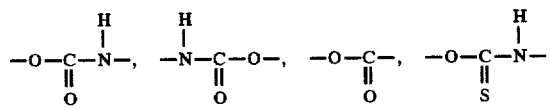

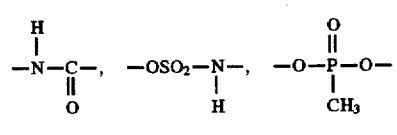

R and Y are the same or different and each represents a saturated or unsaturated aliphatic hydrocarbon group of 10–30 carbon atoms or a saturated or unsaturated fatty acid residue of 10–30 carbon atoms.

2. A composition comprisinq a lipid and a single-stranded nucleic acid copolymer, wherein said lipid is a mixture of a phospholipid and a compound of the following general formula

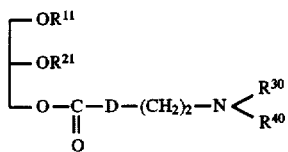

wherein $R^{11}$ and $R^{21}$ are the same or different and each represents oleyl or oleoyl. D represents —$CH_2$— or —NH—. $R^{30}$ and $R^{40}$ are the same or different and each represents methyl or ethyl.

3. A composition according to claim 1, wherein said lipid is a mixture of a phospholipid and a compound selected from the group consisting of 3-O-(4-dimethylaminobutanoyl)-1, 2-O-dioleylglycerol, 3-O-(2-dimethylaminoethyl) carbamoyl-1,2-O-dioleylglycerol, and 2-O-(2-diethylaminoethyl)carbamoyl-1,3-O-dioleoylglycerol.

4. A composition according to claim 1, wherein said phospholipid is selected from the group consisting of phosphatidylethanolamine and phosphatidylcholine.

5. A composition according to claim 1, wherein said single-stranded nucleic acid copolymer is poly(adenylic acid-uridylic acid).

6. A composition according to claim 2, wherein said phospholipid is selected from the group consisting of phosphatidylethanolamine and phosphtidylcholine.

7. A composition according to claim 3, wherein said phospholipid is selected from the group consisting of phosphatidylethanolamine and phosphatidylcholine.

8. A composition according to claim 2, wherein said single-stranded nucleic acid copolymer is poly(adenylic acid-uridylic acid).

9. A composition according to claim 3, wherein said single-stranded nucleic acid copolymer is poly(adenylic acid-uridylic acid).

10. A composition according to claim 4, wherein said single-stranded nucleic acid copolymer is poly(adenylic acid-uridylic acid).

* * * * *